(12) United States Patent  (10) Patent No.: US 8,768,469 B2
Tweden et al.  (45) Date of Patent: Jul. 1, 2014

(54) SYSTEMS FOR REGULATION OF BLOOD PRESSURE AND HEART RATE

(75) Inventors: Katherine S. Tweden, Mahtomedi, MN (US); Richard R. Wilson, Arden Hills, MN (US); Mark B. Knudson, Shoreview, MN (US); Dennis Dong-Won Kim, La Jolla, CA (US); Deepak Bhole, San Diego, CA (US)

(73) Assignee: EnteroMedics Inc., St. Paul, MN (US)

( * ) Notice: Subject to any disclaimer, the term of this patent is extended or adjusted under 35 U.S.C. 154(b) by 1278 days.

(21) Appl. No.: 12/537,019

(22) Filed: Aug. 6, 2009

(65) Prior Publication Data

US 2010/0204741 A1  Aug. 12, 2010

Related U.S. Application Data

(60) Provisional application No. 61/087,557, filed on Aug. 8, 2008.

(51) Int. Cl.
*A61N 1/00* (2006.01)

(52) U.S. Cl.
USPC ............................ 607/44; 607/62; 607/118

(58) Field of Classification Search
USPC ..................... 607/2, 3, 44, 118, 62
See application file for complete search history.

(56) References Cited

U.S. PATENT DOCUMENTS

| 3,650,277 A | 3/1972 | Sjostrand et al. |
|---|---|---|
| 5,707,400 A | 1/1998 | Terry, Jr. et al. |
| 5,891,181 A | 4/1999 | Zhu |
| 6,371,922 B1 | 4/2002 | Baumann et al. |
| 6,522,926 B1 | 2/2003 | Kieval et al. |
| 6,526,318 B1 | 2/2003 | Ansarinia |
| 6,622,041 B2 | 9/2003 | Terry, Jr. et al. |
| 6,668,191 B1 | 12/2003 | Boveja |
| 6,684,105 B2 | 1/2004 | Cohen et al. |
| 6,850,801 B2 | 2/2005 | Kieval et al. |
| 6,957,106 B2 | 10/2005 | Schuler et al. |
| 6,985,774 B2 | 1/2006 | Kieval et al. |
| 7,082,327 B2 | 7/2006 | Houben |
| 7,149,574 B2 | 12/2006 | Yun et al. |
| 7,155,284 B1 | 12/2006 | Whitehurst et al. |
| 7,158,832 B2 | 1/2007 | Kieval et al. |
| 7,167,750 B2 | 1/2007 | Knudson et al. |
| 7,236,822 B2 | 6/2007 | Dobak, III |
| 7,300,449 B2 | 11/2007 | Mische |

(Continued)

FOREIGN PATENT DOCUMENTS

| EP | 0 076 070 A1 | 4/1983 |
|---|---|---|
| WO | WO 2006/023498 A1 | 3/2006 |

(Continued)

OTHER PUBLICATIONS

International Search Report and Written Opinion mailed Oct. 26, 2009.

(Continued)

*Primary Examiner* — Mark W Bockelman

(74) *Attorney, Agent, or Firm* — Merchant & Gould PC

(57) ABSTRACT

A method and apparatus for treating a condition associated with impaired blood pressure and/or heart rate in a subject comprising applying an electrical treatment signal, wherein the electrical treatment signal is selected to at least partially block nerve impulses, or in some embodiments, to augment nerve impulses.

18 Claims, 10 Drawing Sheets

(56) References Cited

U.S. PATENT DOCUMENTS

| | | | |
|---|---|---|---|
| 7,363,076 B2 | 4/2008 | Yun et al. | |
| 7,373,204 B2 | 5/2008 | Gelfand et al. | |
| 7,542,800 B2 | 6/2009 | Libbus et al. | |
| 7,617,005 B2 | 11/2009 | Demarais et al. | |
| 7,620,451 B2 | 11/2009 | Demarais et al. | |
| 7,620,454 B2 | 11/2009 | Dinsmoor et al. | |
| 7,620,455 B2 | 11/2009 | Maschino | |
| 7,630,769 B2 | 12/2009 | Knudson | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,734,355 B2 * | 6/2010 | Cohen et al. | 607/118 |
| 7,756,583 B2 | 7/2010 | Demarais et al. | |
| 7,778,711 B2 | 8/2010 | Ben-David et al. | |
| 7,853,333 B2 | 12/2010 | Demarais | |
| 7,869,881 B2 | 1/2011 | Libbus et al. | |
| 7,873,417 B2 | 1/2011 | Demarais et al. | |
| 7,937,143 B2 | 5/2011 | Demarais et al. | |
| 7,949,398 B1 | 5/2011 | Wenzel et al. | |
| 8,131,371 B2 | 3/2012 | Demarals et al. | |
| 8,140,170 B2 | 3/2012 | Resai et al. | |
| 8,145,316 B2 | 3/2012 | Deem et al. | |
| 8,145,317 B2 | 3/2012 | Demarais et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 8,239,027 B2 | 8/2012 | Imran | |
| 8,260,426 B2 | 9/2012 | Armstrong et al. | |
| 2003/0216792 A1 * | 11/2003 | Levin et al. | 607/48 |
| 2004/0172085 A1 | 9/2004 | Knudson et al. | |
| 2004/0172086 A1 | 9/2004 | Knudson et al. | |
| 2004/0172088 A1 | 9/2004 | Knudson et al. | |
| 2004/0172094 A1 | 9/2004 | Cohen et al. | |
| 2004/0176812 A1 | 9/2004 | Knudson et al. | |
| 2005/0038484 A1 | 2/2005 | Knudson et al. | |
| 2005/0065553 A1 | 3/2005 | Ben Ezra et al. | |
| 2005/0131467 A1 | 6/2005 | Boveja | |
| 2005/0131485 A1 | 6/2005 | Knudson et al. | |
| 2005/0149129 A1 | 7/2005 | Libbus et al. | |
| 2005/0149143 A1 * | 7/2005 | Libbus et al. | 607/44 |
| 2005/0187386 A1 | 8/2005 | Marks et al. | |
| 2005/0228459 A1 | 10/2005 | Levin et al. | |
| 2005/0251212 A1 | 11/2005 | Kieval et al. | |
| 2005/0267542 A1 | 12/2005 | David et al. | |
| 2005/0288730 A1 | 12/2005 | Deem et al. | |
| 2006/0041277 A1 | 2/2006 | Deem et al. | |
| 2006/0079945 A1 | 4/2006 | Libbus | |
| 2006/0089678 A1 | 4/2006 | Shalev | |
| 2006/0095088 A1 | 5/2006 | De Ridder | |
| 2006/0100668 A1 | 5/2006 | Ben-David et al. | |
| 2006/0111754 A1 | 5/2006 | Rezai et al. | |
| 2006/0135998 A1 * | 6/2006 | Libbus et al. | 607/2 |
| 2006/0142801 A1 | 6/2006 | Demarais et al. | |
| 2006/0206150 A1 | 9/2006 | Demarais et al. | |
| 2006/0212076 A1 | 9/2006 | Demarais et al. | |
| 2006/0212078 A1 | 9/2006 | Demarais et al. | |
| 2006/0235474 A1 | 10/2006 | Demarais | |
| 2006/0247737 A1 | 11/2006 | Olson et al. | |
| 2006/0265014 A1 | 11/2006 | Demarais et al. | |
| 2006/0265015 A1 | 11/2006 | Demarais et al. | |
| 2006/0271111 A1 | 11/2006 | Demarais et al. | |
| 2006/0276852 A1 | 12/2006 | Demarais et al. | |
| 2007/0038262 A1 | 2/2007 | Kieval et al. | |
| 2007/0066957 A1 | 3/2007 | Demarais et al. | |
| 2007/0083239 A1 | 4/2007 | Demarais et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0156200 A1 | 7/2007 | Kornet et al. | |
| 2007/0162085 A1 | 7/2007 | DiLorenzo | |
| 2007/0185543 A1 | 8/2007 | Rossing et al. | |
| 2007/0191905 A1 * | 8/2007 | Errico et al. | 607/44 |
| 2007/0203521 A1 | 8/2007 | Dobak et al. | |
| 2007/0203549 A1 | 8/2007 | Demarais et al. | |
| 2007/0208382 A1 | 9/2007 | Yun | |
| 2007/0265687 A1 | 11/2007 | Deem et al. | |
| 2007/0282407 A1 | 12/2007 | Demarais et al. | |
| 2008/0004672 A1 | 1/2008 | Dalal et al. | |
| 2008/0009916 A1 | 1/2008 | Rossing et al. | |
| 2008/0015659 A1 | 1/2008 | Zhang et al. | |
| 2008/0027505 A1 | 1/2008 | Levin et al. | |
| 2008/0051767 A1 | 2/2008 | Rossing et al. | |
| 2008/0077187 A1 | 3/2008 | Levin et al. | |
| 2008/0109043 A1 | 5/2008 | Salo et al. | |
| 2008/0119907 A1 | 5/2008 | Stahmann | |
| 2008/0131467 A1 | 6/2008 | Nelson et al. | |
| 2008/0167699 A1 | 7/2008 | Kieval et al. | |
| 2008/0255642 A1 | 10/2008 | Zarins et al. | |
| 2008/0300645 A1 | 12/2008 | Cholette | |
| 2008/0300646 A1 | 12/2008 | Cholette | |
| 2008/0300648 A1 | 12/2008 | Cholette | |
| 2008/0319513 A1 | 12/2008 | Pu et al. | |
| 2009/0024195 A1 | 1/2009 | Rezai et al. | |
| 2009/0062873 A1 | 3/2009 | Wu et al. | |
| 2009/0076409 A1 | 3/2009 | Wu et al. | |
| 2009/0143838 A1 | 6/2009 | Libbus et al. | |
| 2009/0187230 A1 | 7/2009 | Dilorenzo | |
| 2009/0221939 A1 | 9/2009 | Demarais et al. | |
| 2009/0275997 A1 | 11/2009 | Faltys et al. | |
| 2009/0306465 A1 | 12/2009 | Dudai | |
| 2009/0326613 A1 | 12/2009 | Knoblich | |
| 2010/0004515 A1 | 1/2010 | Houben et al. | |
| 2010/0057150 A1 | 3/2010 | Demarais et al. | |
| 2010/0114244 A1 | 5/2010 | Manda et al. | |
| 2010/0137952 A1 | 6/2010 | Demarais et al. | |
| 2010/0168731 A1 | 7/2010 | Wu et al. | |
| 2010/0168739 A1 | 7/2010 | Wu et al. | |
| 2010/0174282 A1 | 7/2010 | Demarais et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2010/0241183 A1 | 9/2010 | DiLorenzo | |
| 2010/0249773 A1 | 9/2010 | Clark et al. | |
| 2010/0268307 A1 | 10/2010 | Demarais et al. | |
| 2011/0060324 A1 | 3/2011 | Wu et al. | |
| 2011/0112400 A1 | 5/2011 | Emery et al. | |
| 2011/0166499 A1 | 7/2011 | Demarais et al. | |
| 2011/0178570 A1 | 7/2011 | Demarais | |
| 2011/0200171 A1 | 8/2011 | Beetel et al. | |
| 2011/0202098 A1 | 8/2011 | Demarais et al. | |
| 2011/0207758 A1 | 8/2011 | Sobotka et al. | |
| 2011/0208096 A1 | 8/2011 | Demarais et al. | |
| 2011/0208173 A1 | 8/2011 | Sobotka et al. | |
| 2011/0208175 A1 | 8/2011 | Sobotka et al. | |
| 2011/0257564 A1 | 10/2011 | Demarais et al. | |
| 2011/0264011 A1 | 10/2011 | Wu et al. | |
| 2011/0264075 A1 | 10/2011 | Leung et al. | |
| 2012/0022608 A1 | 1/2012 | Libbus et al. | |
| 2012/0022617 A1 | 1/2012 | Tockman et al. | |
| 2012/0053653 A1 | 3/2012 | Hiernaux et al. | |
| 2012/0059431 A1 | 3/2012 | Williams et al. | |
| 2012/0065698 A1 | 3/2012 | Errico et al. | |
| 2012/0071946 A1 | 3/2012 | Errico et al. | |
| 2012/0078319 A1 | 3/2012 | De Ridder | |
| 2012/0083855 A1 | 4/2012 | Gross et al. | |
| 2012/0089047 A1 | 4/2012 | Ryba et al. | |
| 2012/0101413 A1 | 4/2012 | Beetel et al. | |
| 2012/0101538 A1 | 4/2012 | Ballakur et al. | |
| 2012/0101874 A1 | 4/2012 | Ben-Haim et al. | |
| 2012/0116382 A1 | 5/2012 | Ku et al. | |
| 2012/0116383 A1 | 5/2012 | Mauch et al. | |
| 2012/0116486 A1 | 5/2012 | Naga et al. | |
| 2012/0130289 A1 | 5/2012 | Demarais et al. | |
| 2012/0130345 A1 | 5/2012 | Levin et al. | |
| 2012/0130359 A1 | 5/2012 | Turovskiy | |
| 2012/0130360 A1 | 5/2012 | Buckley et al. | |
| 2012/0130458 A1 | 5/2012 | Ryba et al. | |
| 2012/0136344 A1 | 5/2012 | Buckley et al. | |
| 2012/0136350 A1 | 5/2012 | Goshgarian et al. | |
| 2012/0136408 A1 | 5/2012 | Grill et al. | |
| 2012/0136417 A1 | 5/2012 | Buckley et al. | |
| 2012/0136418 A1 | 5/2012 | Buckley et al. | |
| 2012/0143097 A1 | 6/2012 | Pike, Jr. | |
| 2012/0143181 A1 | 6/2012 | Demarais et al. | |

(56) References Cited

U.S. PATENT DOCUMENTS

| | | |
|---|---|---|
| 2012/0143293 A1 | 6/2012 | Mauch et al. |
| 2012/0143294 A1 | 6/2012 | Clark et al. |
| 2012/0150245 A1 | 6/2012 | Rezai et al. |
| 2012/0150267 A1 | 6/2012 | Buckley et al. |
| 2012/0158092 A1 | 6/2012 | Thimineur et al. |
| 2012/0158104 A1 | 6/2012 | Huynh et al. |
| 2012/0172680 A1 | 7/2012 | Gelfand et al. |
| 2012/0172837 A1 | 7/2012 | Demarais et al. |
| 2012/0197198 A1 | 8/2012 | Demarais et al. |
| 2012/0197246 A1 | 8/2012 | Mauch |
| 2012/0197252 A1 | 8/2012 | Deem et al. |
| 2012/0215279 A1 | 8/2012 | Libbus |
| 2012/0221072 A1 | 8/2012 | Fukamachi et al. |
| 2012/0232610 A1 | 9/2012 | Soffer et al. |
| 2012/0232613 A1 | 9/2012 | Kieval et al. |
| 2012/0239108 A1 | 9/2012 | Foutz et al. |
| 2012/0245656 A1 | 9/2012 | Brockway et al. |
| 2012/0253336 A1 | 10/2012 | Littrup et al. |
| 2012/0253378 A1 | 10/2012 | Makower et al. |
| 2012/0259380 A1 | 10/2012 | Pyles |
| 2012/0290024 A1 | 11/2012 | Zhang et al. |
| 2012/0296232 A1 | 11/2012 | Ng |
| 2012/0296329 A1 | 11/2012 | Ng |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023862 A1 | 1/2013 | Marrouche et al. |

FOREIGN PATENT DOCUMENTS

| | | |
|---|---|---|
| WO | 2007092330 A1 | 8/2007 |
| WO | WO 2009/131639 | 10/2009 |
| WO | 2012044472 A2 | 4/2012 |
| WO | 2012060874 A2 | 5/2012 |
| WO | 2012154800 A1 | 11/2012 |

OTHER PUBLICATIONS

Balmain et al., "Differences in arterial compliance, microvascular function and venous capacitance between patients with heart failure and either preserved or reduced left ventricular systolic function," *The European Journal of Heart Failure* 9:865 (2007).

Benthem et al., "Excess portal venous long-chain fatty acids induce syndrome X via HPA axis and sympathetic activation," *Am. J. Physiol. Endocrinol. Metab.* 279: E1286, 2000.

Bernal-Mizrachi, C. et al., "An Afferent Vagal Nerve Pathway Links Hepatic PPARα Activation to Glucocorticoid-Induced Insulin Resistance and Hypertension," *Cell Metabolism*, vol. 5, pp. 91-102 (Feb. 2007).

Camilleri, M. et al., "Intra-abdominal vagal blocking (VBLOC therapy): Clinical results with a new implantable medical device," *Surgery*, vol. 143, No. 6, pp. 723-731 (Jun. 2008).

Camilleri, M. et al., "Selection of electrical algorithms to treat obesity with intermittent vagal block using an implantable medical device," *Surgery for Obesity and Related Diseases*, vol. 5, pp. 224-230 (2009).

Camilleri, M. et al., "Vagal Blocking for Obesity Control (Vbloc): Plasma Pancreatic Polypeptide (PPP) Response to a Standarized Sham Meal Challenge," *Obesity*, vol. 15, Supplement, Abstract No. 20-OR, pp. A6-A7 (Sep. 2007).

Eguchi et al., "Cardiovascular prognosis of sustained and white-coat hypertension in patients with type 2 diabetes mellitus," *Clinical Methods and Pathology*, 13:15-20 (2008).

Fonarow et al., "Characteristics, Treatments, and Outcomes of Patients with Preserved Systolic Function Hospitalized for Heart Failure," *Journal of the American College of Cardiology*, 50:768 (2007).

Grekin et al., *Hypertension* 26:193 (1995).

Herrera et al., *Obesity Surgery* 18:946 (2008).

Kow et al., *Obesity Surgery*, 18:924 (2008).

Kow et al., *Obesity Surgery*, 18:914 (2008).

Lin, "Ghrelin acts at the nucleus of the solitary tract to decrease arterial pressure in rats," *Hypertension*, May 2004; 43(5):977-82.

McMurray et al., "Heart failure with preserved ejection fraction: Clinical characteristics of 4133 patients enrolled in the I-Preserve trial," *European Journal of Heart Failure* 10 (2008) 149-156.

Merck Manual, 18th Edition, 2006, 652-672.

Moran et al., "Differential Effects of Ramipril on Ambulatory Blood Pressure in African Americans and Caucasians," *AJH* 20:884 (2007).

Ng et al., "Effects of direct sympathetic and vagus nerve stimulation on the physiology of the whole heart—a novel model of isolated Langendorff perfused rabbit heart with intact dual autonomic innervation," *Experimental Physiology*, 86:319 (2001).

Ouzounian et al., "Diastolic heart failure: mechanisms and controversies," *Nature Clinical Practice* (2008) pp. 1-12.

Pickering et al., "Ambulatory Blood-Pressure Monitoring," *New England Journal of Medicine*, 354:22 (2006).

Pickering et al., "New Ways of Measuring Blood Pressure," *AJH* 19:988 (2006).

The Seventh Report of the Joint National Committee on Prevention, Detection, Evaluation, and Treatment of High Blood Pressure, U.S. Department of Health and Human Services, NIH Publication No. 04-5230, Aug. 2004.

Solomonow et al., "Control of muscle Contractile Force through Indirect High-Frequency Stimulation," *Am. J. of Physical Medicine*, vol. 62, No. 2, pp. 71-82 (1983).

Toouli, J. et al., "Intra-Abdominal Vagal Blocking Reduces Calorie Intake, Enhances Satiation and Reduces Hunger During Significant and Sustained Weight Loss," *Gastroenterology*, vol. 134, No. 4, Suppl. 1, Abstract No. M1255, p. A-370, (Apr. 2008).

Toouli, J. et al., "Vagal blocking for obesity control (VBLOC): Effects on excess weight loss, calorie intake, satiation and satiety," *Obesity Surgery*, vol. 17, Abstract No. 83, p. 1043 (2007).

Tweden, K. et al., "Vagal Blocking for Obesity Control (VBLOC): Concordance of Effects of Very High Frequency Blocking Current at the Neural and Organ Levels Using Two Preclinical Models," *Gastroenterology*, vol. 130, No. 4, Suppl. 2, Abstract No. 951, p. A-148 (Apr. 2006).

Tweden et al., *Obesity Surgery* (2006) 16:988.

Vozarova de Courten et al., "Parasympathetic Blockade Attenuates Augmented Pancreatic Polypeptide But Not Insulin Secretion in Pima Indians," *Diabetes*, 53:663, Mar. 2004.

Wang, "Effects of intravenous fentanyl on spontaneous renal sympathetic nerve activity in normal and vagotomized rabbits," *Chin. Med. Sci. J.* Dec. 19, 2004(4):282-5.

Weck, "Treatment of hypertension in patients with diabetes mellitus: relevance of sympathovagal balance and renal function," *Clin. Res. Cardiol.* Oct. 2007 96(10):707-18.

Wenzel, Drugs, Vo. 65, Suppl. 2:29-39 (2005).

Wilson, R. et al., "Intra-Abdominal Vagal Blocking Reduces Body Weight with Associated Reductions in Heart Rate and Without Adverse Effects on Electrocardiographic Parameters," *Obesity Surgery*, vol. 18, Abstract No. O53, p. 923 (2008).

Examination Report mailed Aug. 19, 2013, for related Japanese patent application No. 2011-522270.

Herrera, et al., "Intermittent Vagal Blocking with An Implantable Device Reduces Maximum Tolerated Volume (MTV) During a Standardized Nutrient Drink Test in Obese Subjects," AGA Institute, AASLD, SSAT, The 110th Annual Meeting of the AGA Institute: Digestive Disease Week May 30-Jun. 4, 2009, Chicago, IL, Gastroenterology vol. 136, No. 5, Suppl. 1 (May 2009).

Brancatisano, et al., "Implantation Technique of a Novel Vagal Blockade Medical Device for the Treatment of Obesity," IFSO-APC OSSANZ Conference 2008: Mar. 25-27, 2009, Hilton Cairns, Queensland Conference Program Handbook.

Toouli, M.D., et al., "Intra-Abdominal Vagal Blocking Reduces Calorie Intake, Enhances Satiation and Reduces Hunger during Significant and Sustained Weight Loss in Obese Subjects," Digestive Disease Week and the 109th Annual Meeting of the AGA Institute: May 17-22, 2008, San Diego, CA, Gastroenterology vol. 134, No. 4 (Suppl. 1) p. A-370 (Apr. 2008).

Tweden, et al. "Vagal Blocking for Obesity Control (VBLOC): Studies of Pancreatic Function and Safety in a Porcine Model," Obesity Surgery: Including Laparoscopy and Allied Care, Program Issue,

(56) References Cited

OTHER PUBLICATIONS

World Congress, Australia, Aug. 30-Sep. 2, 2006. An International Surgical Journal for Research and Treatment of Massive Obesity, vol. 16, No. 8, p. 988, Aug. 2006.

Toouli, et al., "Vagal Blocking for Obesity Control (VBLOC): Effects on Excess Weight Loss, Calorie Intake, Satiation and Satiety," Obesity Surgery: Including Laparoscopy and Allied Care, Program Issue, World Congress, Porto, Sep. 5 to 8, 2007. An International Surgical Journal for Research and Treatment of Massive Obesity, vol. 17, No. 8, p. 1043 Aug. 2007.

Kow, et al., "Comparison of Food Ingestion Disorders with Three Devices for Obesity," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, pp. 914-915 Aug. 2008.

Wilson, et al., "Intra-Abdominal Vagal Blocking Reduces body Weight with Associated Reductions in Heart Rate and Without Adverse Effects on Electrocardiographic Parameters," Obesity Surgery: Including Laparoscopy and Allied Care, Program and Abstracts of the 13th World Congress of IFSO Buenos Aires, Argentina, Sep. 24-27, 2008. An International Surgical Journal for Research and Treatment of Massive Obesity, vol. 18, No. 8, p. 923 Aug. 2008.

Kow, et. al. "Selecting Vagal Blocking Electrical Algorithms for Obesity Treatment," Obesity Surgery: Including Laparascopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, p. 924, Aug. 2008.

Herrera, et al., "VBLOC and Improvements in Co-Morbidities in Obese Subjects During Weight Loss," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 983-984, Aug. 2009.

Herrera, et al., "Intermittent Vagal Blocking with an Implantable Device Reduces Maximum Tolerated Volume (MTV) During a Standardized Nutrient Drink Test in Obese Subjects," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 1012 Aug. 2009.

Brancastisano, et al., "Empower: A 12-Month Randomized, Prospective Clinical Trial: Safety and Effectiveness of VBLOC Therapy," 23rd Annual Scientific Conference of the Obesity Surgery Society of Australia and New Zealand, OSSANZ Conference 2010: The Changing Shape of Bariatrics, Nov. 10-12, Wednesday Nov. 10 10:30 am-12 noon, Tasmania Hotel Grand Chancellor, Hobart, Conference Program Handbook.

Kow, et al., "Vagal Blocking Improves Obesity-Related Co-Morbidities in Obese Subjects with type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Wednesday Nov. 10 3:30 pm- 5:00 pm, Tasmania Hotel Grand Chancellor, Hobart, Conference Program Handbook.

Collins, et al., "Reduces Calorie Intake and Weight Loss during Vagal Block (VBLOC Therapy) in Morbidly Obese Patients with Type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Thursday Nov. 11 10:30 am- 12 noon, Tasmania Hotel Grand Chancellor, Hobart, Conference Program Handbook.

Toouli, et al., "Vagal Blocking: Treatment of Obesity Related type 2 Diabetes and blood Pressure—18 Month Results," 24th Annual Scientific Conference of the Obesity Surgery Society of Australia and New Zealand, OSSANZ Conference 2012: Bariatric surgery-more than an operation, Apr. 11-13, Wednesday Nov. 11 3:30 pm- 5:00 pm, Northern Territory Darwin Convention Centre, Darwin, Conference Program Handbook.

Tweden, et al., "Vagal Blocking for Obesity Control (VBLOC): Studies of Pancreatic and Gastric Function and Safety in a Porcine Model," Plenary Session 2006/2 Surgery for Obesity and Related Diseases, Official Journal of the American Society for Bariatric Surgery, vol. 2, No. 3, pp. 301-302, May/Jun. 2006.

Camilleri, et al., "Selection of Electrical Algorithms to Treat Obesity with Intermittent Vagal Block Using an Implantable Medical Device," Surgery for Obesity and Related Diseases, Official Journal of the American Society for Bariatric Surgery, vol. 5, No. 2, pp. 224-229, Mar./Apr. 2009.

Herrera, et al., "Intermittent Vagal Blockade with an Implantable Device Improves Glycemic Control in Obese subjects with Type 2 Diabetes," 2009 Poster Session / Supplement to Surgery for Obesity and Related Diseases, Official Journal of the American Society for Bariatric Surgery, vol. 5, No. 3S, pp. S48-S49, May/Jun. 2009.

Herrera, et al., "Vagal Blocking Improves Glycemic Control and Blood Pressure in Subjects with Type 2 Diabetes and Hypertension," 2010 Plenary Session / Supplement to Surgery for Obesity and Related Diseases, Official Journal of the American Society for Bariatric Surgery, vol. 2, No. 3, pp. S1-S26, May/Jun. 2010.

Camilleri, et al., "Vagal Blocking for Obesity control (VBLOC): Plasma Pancreatic Polypeptide (PPP) Response to a Standardized Sham Meal Challenge," The Obesity Society 2007 Annual Scientific Meeting, Oct. 20-24, 2007, New Orleans Louisiana. Supplement to Obesity, vol. 15, Program Abstract Supplement, Sep. 2007.

Camilleri, et al., "Intra-abdominal Vagal Blocking (VBLOC therapy): Clinical Results with a New Implantable Medical Device," Surgery, vol. 143, No. 6, pp. 723-731, Jun. 2008.

Kow, et al., "Vagal Blocking for the Treatment of Obesity Delivered Using the Fully Implantable Maestro Rechargeable System: 12 Month Results," Surgery for Obesity and Related Diseases: Emerging Technologies Session 2011, 7, pp. 363-364, 2011.

Sarr, et al., "The EMPOWER Study: Randomized, Prospective, Double-Blind, Multicenter Trial of Vagal Blockade to Induce Weight Loss in Morbid Obesity," Obes. Surg. Published Sep. 8, 2012, (12pp) Springer Science +Business Media, LLC (2012).

Tweden, et al., "Vagal Blocking Treatment of Obesity Related Type 2 Diabetes and Blood Pressure—18 Month Results,"5th Congress of the International Federation for the surgery of Obesity and Metabolic Disorders European Chapter (IFSO-EC), Barcelona '12, Apr. 26-28, 2012.

Toouli, et al., "Vagal Blocking for Obesity Control (VBLOC): Interim Six Months Results in an ongoing Trial Using a Second Generation System," 2008 Scientific Session of the Society of American Gastrointestinal and Endoscopic (SAGES), Philadelphia, Pennsylvania, USA Apr. 9-12, 2008. Poster Presentations, Surgical Endoscopy (2008) 22, p. S194, Springer Science+Business Media, LLC (2008).

Toouli, et al., "Vagal Blocking for Obesity Control (VBLOCTM): Ongoing Comparison of Weight Loss with Two Generations of an Active, Implantable Medical Device," 2008 Plenary Session II / Surgery for Obesity and Related Diseases, Official Journal of the American Society for Bariatric Surgery, e t al., vol. 4, No. 3, p. 305, May/Jun. 2008.

Waataja, et al., "Effects of High-Frequency Alternating Current on Axonal Conduction Through the Vagus Nerve," Journal of Neural Engineering Neural Eng. 8 (2011) (1741-1747) IOP Publishing Ltd, (2011) online at stacks.iop.org.

Kow, et al., "Comparison of Food Ingestion disorders with Three Devices for Obesity Treatment," and Wilson, Richard, et al., "Intra-abdominal Vagal Blocking Reduces Body Weight with Associated Reductions in Heart Rate and Without Adverse Effects on Electrocardiographic Parameters," TOS 2008 Abstract Supplement / Poster Session 2 Abstracts, vol. 16, Supp. 1: S222, Oct. 2008 www.obesityjournal.org.

Herrera, et al., "Treatment of Obesity-Related Type 2 Diabetes with Vagal Blocking," Obesity 2011 Abstract Supplement / Poster Abstracts—Monday, Oct. 3, 2011, Obesity vol. 19, sup. 1:S185, Nov. 2011, www.obsesityjournal.org.

Wray, et al., "Reduced Calorie Intake and Weight Loss During Vagal Blocking in Subjects with Obesity-Related Type 2 Diabetes Mel-

(56) References Cited

OTHER PUBLICATIONS litus," Obesity 2011 Abstract Supplement / Poster Abstracts—Monday, Oct. 3, 2011, Obesity vol. 19, Supp. 1:S190, Nov. (2011), www.obesityjournal.org.

Toouli, et al., "Reduced Calorie Intake and Weight Loss During Vagal Bloc (VBLOC Therapy) in Morbidly Obese Patients with Type 2 Diabetes Mellitus," Gastroenterology 2011, vol. 140: S-619, AGA Institute.

Tweden, et al., "Vagal Blocking for Obesity Control (VBLOC): Concordance of Effects of Very High Frequency Blocking Current At the Neural and Organ Levels Using Two Preclinical Models," Gastroenterology 2006, vol. 130 (suppl2 2) A-148, AGA Institute.

Kow, et al., "An Implantable Vagal Blocking System to Treat Obesity: Laparoscopic Implantation Technique and Early Results in a proof-of-Principle Clinical Study,", SAGES 2008 Emerging Technology Oral Abstracts, p. 295, www.sages.org.

Toouli, et al., "Treatment of Obesity-Related Co-Morbidities with VBLOC Therapy," Obes. Surg. 21:998, Springer Science+Business Media, LLC (2011).

International Search Report and Written Opinion from related related PCT patent application PCT/US2009/053114 mailed Oct. 26, 2009.

Thames, et al. "Impaired cardiopulmonary baroreflex control of renal nerves in renal hypertension," Circulation Research—Journal of the American Heart Association, 57: 741-747. (1985).

Vozarova De Courten, et al., "Parasympathetic Blockade Attenuates Augmented Pancreatic Polypeptide But Not Insulin Secretion in Pima Indians," Diabetes, 53:663, Mar. 2004.

Zanger, et al., "Structure-Activity Relationship and Drug Design," Remington Pharmaceutical Sciences, Ed. 16, Chap 27, pp. 420-425 (1980).

Hao, "A Programmable Implantable Neural Stimulation System," Space Medicine & Medical Engineering 21 (2):147-151 (Apr. 2008).

Brinkmann, et al., "Catheter-Based Renal Nerve Ablation and Centrally Generated Sympathetic Activity in Difficult-to-Control Hypertensive Patients: Prospective Case Series," Hypertension, 60:1485-1490, (Dec. 2012).

\* cited by examiner

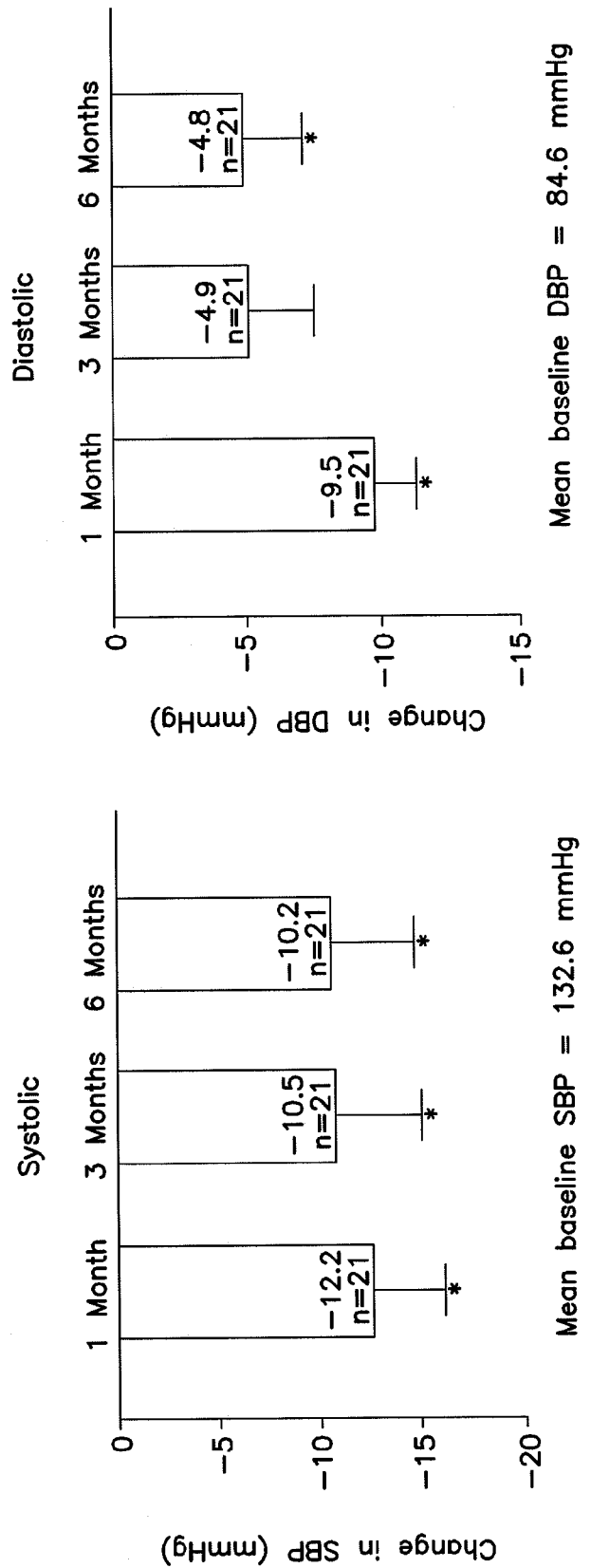

FIG. 8

Blood Pressure - Shift Tables

Systolic

| Visit | Baseline SBP<130 mmHg N=15 | | Baseline SBP ≥ 130 mmHg N=11 | |
|---|---|---|---|---|
| | SBP<130 mmHg | SBP ≥ 130 mmHg | SBP<130 mmHg | SBP ≥ 130 mmHg |
| 6 months | 13 | 2 | 7 | 4 |

Diastolic

| Visit | Baseline DBP<80 mmHg N=9 | | Baseline DBP ≥ 80 mmHg N=17 | |
|---|---|---|---|---|
| | DBP<80 mmHg | DBP ≥ 80 mmHg | DBP<80 mmHg | DBP ≥ 80 mmHg |
| | 8 | 1 | 7 | 10 |

SYSTEMS FOR REGULATION OF BLOOD PRESSURE AND HEART RATE

CROSS-REFERENCE TO RELATED APPLICATIONS

This application claims benefit of Provisional Application No. 61/087,557, filed Aug. 8, 2008, which application is incorporated herein by reference.

BACKGROUND OF THE INVENTION

It is estimated that approximately 50 million people in the US have high blood pressure. The criteria for diagnosis of hypertension has changed: a blood pressure of 120/80 mm Hg is considered normal; 120-139 or 80-89 mmHg is defined as pre-hypertensive; greater than or equal to 140-159 mm Hg systolic or 90-99 mm Hg diastolic is stage I hypertension; and greater than or equal to 160 mm Hg systolic or greater than or equal to 100 mm Hg diastolic is stage II hypertension. (The Seventh Report of the Joint National Committee on Prevention, Detection, Evaluation and Treatment of High Blood Pressure, (JNC 7), NHLBI publication, Hypertension 42:1206, 2003). Of those who have been diagnosed, about two thirds do not achieve blood pressure control of less than 140/90 mm Hg, and nearly 15% receive no treatment at all. About half of the people with hypertension never know they have high blood pressure because of the lack of specific symptoms. In most cases of hypertension, the cause is unknown, so the diagnosis is called primary hypertension. In about 5 to 10 percent of people, high blood pressure is a secondary symptom of some other medical condition. For example, there might be an organic cause such as kidney disease, tumor of the adrenal glands, heart defects, or disorders of the nervous system.

Aggressive drug treatment of long-term high blood pressure can significantly reduce the incidence of death from heart disease and other causes in both men and women. In people with diabetes, controlling both blood pressure and blood glucose levels prevents serious complications of that disease. If patients have mild hypertension and no heart problems, then lifestyle changes may suffice to control the condition. For more severe hypertension or for mild cases that do not respond to changes in diet and lifestyle within a year, drug treatment is usually necessary. A single-drug regimen is usual to control mild to moderate hypertension. More severe hypertension often requires a combination of two or more drugs. Prolonged-release drugs are being developed so that they are most effective during early morning periods, when patients are at highest risk for heart attack or stroke.

It is very important to rigorously maintain a drug regimen. Patients who discontinue antihypertensive therapy, particularly smokers and younger adults, are at a significantly increased risk for stroke. All drugs used for hypertension have side effects. Common side effects include fatigue, coughing, skin rash, sexual dysfunction, depression, cardiac dysfunction, or electrolyte abnormalities. Because of these side effects finding the best drug for the patient while encouraging ongoing patient compliance may be difficult.

Congestive heart failure (CHF) is a condition where the heart pump efficiency (cardiac output) of the heart becomes so low that blood circulation is inadequate to meet tissue needs. Congestive heart failure is usually a progressively worsening condition resulting in serious disability and death. Approximately five million Americans, with a significant percentage being under the age of 60 years, suffer from CHF. Past research suggests that a slowing an elevated heart rate can improve heart performance.

Despite the availability of many therapies, hypertension and congestive heart failure remain major health issues. Many of the therapies have undesirable side effects, or do not achieve adequate control of blood pressure or heart rate. Thus, there remains a need to develop systems and methods for regulating blood pressure and/or heart rate.

SUMMARY

The disclosure provides systems and methods for treating conditions relating to impaired blood pressure and/or heart rate control. In embodiments, a method of treating a condition associated with impaired heart rate and/or blood pressure in a subject comprises applying an intermittent electrical treatment signal to a target nerve or tissue in proximity to the target nerve of the subject having impaired heart rate and/or blood pressure regulation, wherein said electrical treatment signal is selected to at least partially down-regulate neural activity on the nerve during an on time and to at least partially restore neural activity on the nerve during an off time. The method can be applied to treat hypertension and/or congestive heart failure.

In some embodiments, the electrical treatment signal is applied to the vagus nerve and the electrical signal is selected for frequency, pulse width, amplitude and timing. In some embodiments, the electrical signal is applied intermittently in a cycle including an on time of application of the signal followed by an off time during which the signal is not applied to the nerve, wherein the on and off times are applied multiple times per day over multiple days. The systems and devices of the disclosure can be combined with a drug treatment. Systems comprise a device that is programmed to deliver an electrical treatment signal with characteristics of frequency, on and off times, amplitude, location, nerve, selected to provide for control of blood pressure and/or heart rate.

BRIEF DESCRIPTION OF THE DRAWINGS

FIG. 7C shows the effect of electrical signal therapy on the change in blood pressure for subjects with elevated blood pressure completing 6 months of therapy. The cohort included patients who had systolic pressure greater than or equal to 140 mmHg and/or diastolic pressure greater than or equal to 90 mmHg and were not diabetic; were diabetic and had systolic pressure of greater than or equal to 130 and/or diastolic pressure greater than 80 mmHg; were diagnosed with hypertension at the time of implantation; or did not have diabetes and had Pre-hypertension with a systolic pressure of 120-139 and/or diastolic pressure of 80-89. The mean baseline systolic pressure was 132.6 mmHg and the mean baseline diastolic pressure was 84.6 mm Hg. Significant changes were seen in subjects with hypertensive baseline systolic blood pressure (SBP) and diastolic blood pressure (DBP) at all time points. The asterisk denotes that the P value is significant for change from baseline+/−SEM.

FIG. 8 shows the shift in blood pressure in patients with and without elevated blood pressure at 6 months of therapy.

DETAILED DESCRIPTION

Figure 1:
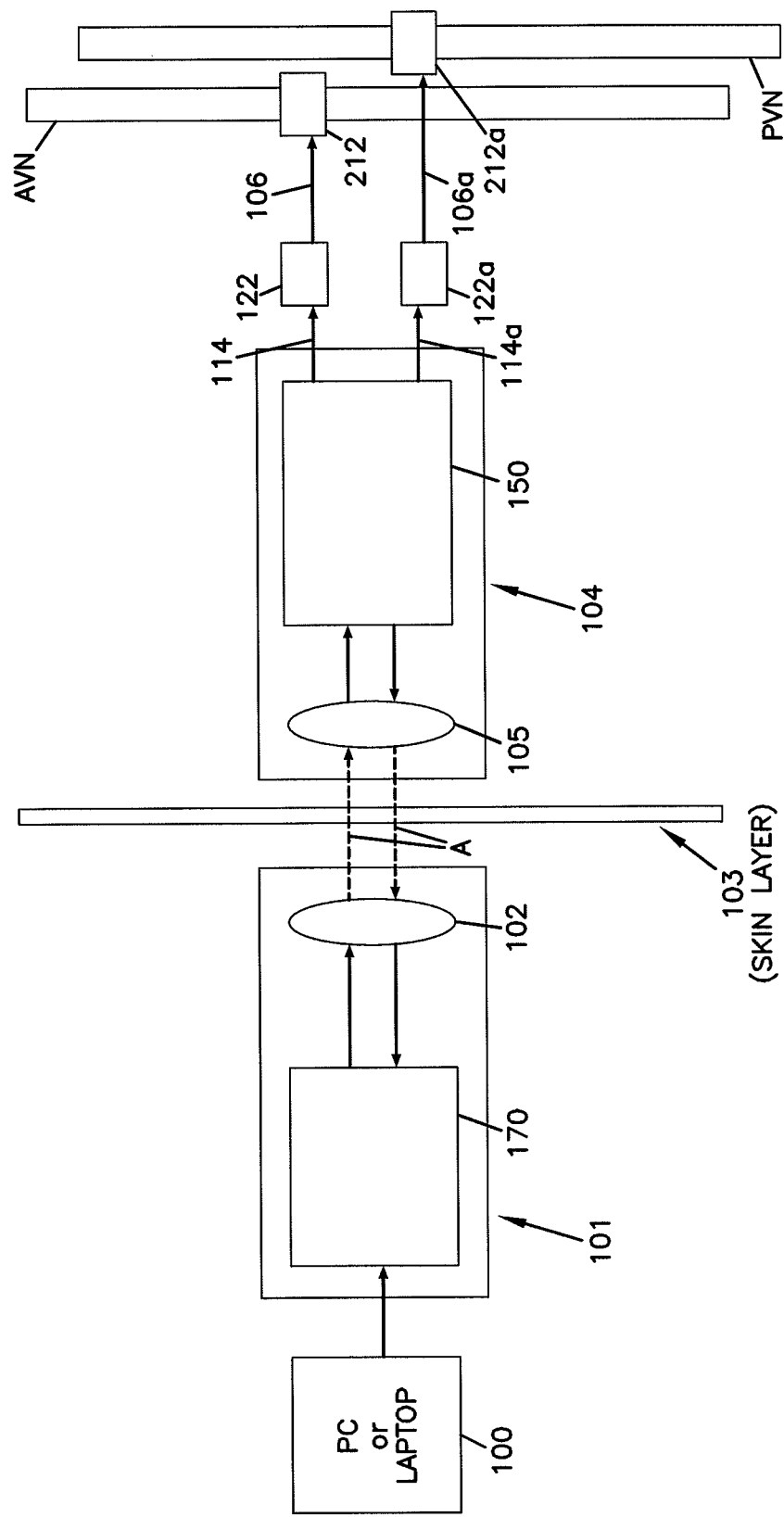
FIG. 1 is a schematic representation of an implantable system configuration for applying an electrical signal to a vagus nerve.

The following commonly assigned patent and U.S. patent applications are incorporated herein by reference: U.S. Pat. No. 7,167,750 to Knudson et al. issued Jan. 23, 2007; US 2005/0131485 A1 published Jun. 16, 2005, US 2005/0038484 A1 published Feb. 17, 2005, US 2004/0172088 A1 published Sep. 2, 2004, US 2004/0172085 A1 published Sep. 2, 2004, US 2004/0176812 A1 published Sep. 9, 2004 and US 2004/0172086 A1 published Sep. 2, 2004. Also incorporated herein by reference is International patent application Publication No. WO 2006/023498 A1 published Mar. 2, 2006.

This disclosure includes systems and methods for regulating heart rate and/or blood pressure in a subject. In embodiments, a method of treating a condition associated with elevated blood pressure and/or heart rate in a subject comprises applying an intermittent neural conduction signal to a target nerve of the subject, with said neural conduction signal selected to down-regulate neural activity on the nerve and to at least partially restore neural activity on the nerve upon discontinuance of said block. In some embodiments, the target nerve is the vagus nerve. In some embodiments, the signal is applied below the vagal innervation of the heart. In some embodiments, the electrical signal is selected for frequency, amplitude, pulse width, and timing. The electrical signal may also be further selected to regulate heart rate and/or blood pressure. In some embodiments, the signal is selected for down regulation of neural activity in order to decrease systolic and/or diastolic blood pressure. In other embodiments, a signal may be applied to upregulate neural activity in order to increase blood pressure. In some embodiments, the parameters of the electrical signal treatment are selected in order to decrease heart rate.

A. Neural Control of Heart Rate and/or Blood Pressure

Hypertension is a cause of heart disease and other related cardiac co-morbidities. Hypertension is a major risk factor for major cardiac events and is associated with mortality due to cardiac events. Hypertension generally relates to high blood pressure, such as a transitory or sustained elevation of systemic arterial blood pressure to a level that is likely to induce cardiovascular damage or other adverse consequences. Hypertension has been defined as a systolic blood pressure equal to or above 140 mm Hg and/or a diastolic blood pressure equal to or above 90 mm Hg, or for diabetic patients a systolic blood pressure equal to or above 130 mm Hg and/or a diastolic blood pressure equal to or above 80 mm Hg. Mean arterial pressure (MAP) takes into account pulsatile blood flow in the arteries and is the best measure of perfusion pressure to organs. Pre-hypertension has been defined as a systolic blood pressure of 120 to 139 mmHg and/or a diastolic blood pressure of 80-90 mm Hg. (JNC 7, cited supra) When blood vessels constrict, hypertension occurs and the heart works harder to maintain flow at a higher blood pressure. Consequences of uncontrolled hypertension include, but are not limited to, retinal vascular disease, stroke, left ventricular hypertrophy and failure, stroke, myocardial infarction, dissecting aneurysm, and renovascular disease.

Heart failure occurs when the heart is incapable of maintaining sufficient blood flow to accommodate tissue perfusion and metabolic requirements. Hypertension precedes heart failure in 90% of the cases and increases the risk of heart failure by two to three fold. Drug treatment with some classes of blood pressure medication is useful for controlling disease progression. Controlling blood pressure is one way heart failure is treated. Decreasing systolic blood pressure has been shown to be uniformly beneficial. (JNC 7 at page 35, cited supra).

Other disease conditions in which control of blood pressure and/or heart rate play a role include coronary artery disease, ischemic heart disease, diabetes, chronic kidney disease, and cerebrovascular disease. The treatment of these conditions often includes treatment with drugs to lower blood pressure. (JNC 7; cited supra).

The autonomic nervous system (ANS) regulates "involuntary" actions, while the contraction of voluntary (skeletal) muscles is controlled by somatic motor nerves. Examples of organs subject to involuntary actions include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels. Both heart rate and blood pressure are controlled via the ANS.

The ANS includes, but is not limited to, the sympathetic nervous system, the enteric nervous system, and the parasympathetic nervous system. The sympathetic nervous system is affiliated with the "fight or flight response" resulting in increases in blood pressure and heart rate to increase skeletal muscle blood flow, and decreases in digestion to provide the energy. The enteric nervous system, sometimes called the second brain, controls the stomach, intestines, and many gastrointestinal functions. The parasympathetic nervous system is affiliated with controlling body functions and decreases blood pressure and heart rate, and increases digestion and manages energy balance.

The cardiovascular (CV) center is located in the medullary center in the brain and controls cardiovascular functions such as heart rate, contractility, and blood vessels. The cardiovascular center receives input from the higher centers in the brain and from afferent fibers of the sympathetic and parasympathetic nerves, including the vagus nerve. The CV center decreases heart rate and can cause vasodilation by parasympathetic activity via efferent impulses carried by the vagus nerve. The CV center can also increase heart rate and cause vasoconstriction via sympathetic stimulation. The major portion of the parasympathetic cranial outflow is via the vagus nerves.

The vagus transmits a diverse array of signals to the central nervous system (CNS) that influence the regulation of cardio- and vaso-motor function and blood pressure, heart rate, neuroimmune modulation, endocrine function as well as gastrointestinal function. For example, the CNS integrates signals from peripheral sites like the liver to modulate blood pressure and glucose. (Bernal-Mizrachi et al, Cell Metabolism 5:91-102, 2007). Infusion of long-chain fatty acids into the portal vein, a major conduit to the liver, has effects that suggest involvement of the CNS including increases in circulating levels of epinephrine and norepinephrine, elevated blood pressure, and accelerated hepatic glucose production (Benthem et al., Am. J. Physio. Endocrin. Metab. 279:E1286-E1293, 2000; Grekin et al., Hypertension 26:193-198, 1995). Hepatic signals are likely transmitted to the CNS by the vagus nerve since vagal activity is increased by portal or jejunal infusion of lipids. The vagus nerve and sympathetic nerves innervate the heart and the blood vessels near the heart. Neural signals from the vagus nerve and other nerves such as the glossopharyngeal nerve, cranial sinus nerve all may influence heart rate and/or blood pressure. In the brainstem, the vagus afferent signals are relayed and influence many of the brainstem cardiovascular control areas that modulate blood pressure and heart rate.

B. Therapy Delivery Equipment

The disclosure provides systems and devices for regulating blood pressure and/or heart rate comprising an impulse generator that provides signals to modulate neural activity on the vagus nerve. The systems and methods are useful, inter alia, in treating hypertension, pre hypertension, congestive heart failure, and hypertension associated with coronary artery disease, ischemic heart disease, chronic kidney disease, diabetes, and cerebrovascular disease.

In an embodiment, a system (schematically shown in FIG. 1) for treating such conditions as hypertension, and/or congestive heart failure includes an impulse generator (also referred to as neuroregulator) 104, an external mobile charger 101, and two electrical lead assemblies 106, 106a. The impulse generator 104 is adapted for implantation within a patient to be treated. In some embodiments, the impulse generator 104 is implanted just beneath a skin layer 103.

In some embodiments, the lead assemblies 106, 106a are electrically connected to the circuitry of the impulse generator 104 by conductors 114, 114a. Industry standard connectors 122, 122a are provided for connecting the lead assemblies 106, 106a to the conductors 114, 114a. As a result, leads 116, 116a and the impulse generator 104 may be separately implanted. Also, following implantation, lead 116, 116a may be left in place while the originally placed impulse generator 104 is replaced by a different impulse generator.

The lead assemblies 106, 106a provide electrical signals that up-regulate and/or down-regulate nerves of a patient based on the therapy signals provided by the impulse generator also referred to as a neuroregulator 104. In an embodiment, the lead assemblies 106, 106a include distal electrodes 212, 212a, which are placed on one or more nerves of a patient. For example, the electrodes 212, 212a may be individually placed on the vagal trunks of a patient. For example, the leads 106, 106a have distal electrodes 212, 212a which are individually placed on the anterior and posterior vagal nerves AVN, PVN, respectively, of a patient, for example, just below the patient's diaphragm. Fewer or more electrodes can be placed on or near fewer or more nerves. In some embodiments, the electrodes are cuff electrodes.

Other electrodes can be placed on the vagus nerve on a location near the SA node of the heart, the carotid sinus or the aortic arch. Electrodes may also be placed intravascularly in the ascending aorta or carotid arteries. In some embodiments, an electrode may be placed on the vagus nerve at a subdiaphragmatic location and another electrode placed on the right vagus nerve near the SA node of the heart or in the tissue surrounding the glossopharyngeal nerve or cardiac sinus nerve. In other embodiments, an electrode may be placed on the vagus nerve at a supradiaphragmatic location.

The external mobile charger 101 includes circuitry for communicating with the implanted neuroregulator (impulse generator) 104. In some embodiments, the communication is a two-way radiofrequency (RF) signal path across the skin 103 as indicated by arrows A. Example communication signals transmitted between the external charger 101 and the neuroregulator 104 include treatment instructions, patient data, and other signals as will be described herein. Energy or power also can be transmitted from the external charger 101 to the neuroregulator 104 as will be described herein.

In the example shown, the external charger 101 can communicate with the implanted neuroregulator 104 via bidirectional telemetry (e.g. via radiofrequency (RF) signals). The external charger 101 shown in FIG. 1 includes a coil 102, which can send and receive RF signals. A similar coil 105 can be implanted within the patient and coupled to the neuroregulator 104. In an embodiment, the coil 105 is integral with the neuroregulator 104. The coil 105 serves to receive and transmit signals from and to the coil 102 of the external charger 101.

For example, the external charger 101 can encode the information as a bit stream by amplitude modulating or frequency modulating an RF carrier wave. The signals transmitted between the coils 102, 105 preferably have a carrier frequency of about 6.78 MHz. For example, during an information communication phase, the value of a parameter can be transmitted by toggling a rectification level between half-wave rectification and no rectification. In other embodiments, however, higher or lower carrier wave frequencies may be used.

In an embodiment, the neuroregulator 104 communicates with the external charger 101 using load shifting (e.g., modification of the load induced on the external charger 101). This change in the load can be sensed by the inductively coupled external charger 101. In other embodiments, however, the neuroregulator 104 and external charger 101 can communicate using other types of signals.

In an embodiment, the neuroregulator 104 receives power to generate the therapy signals from an implantable power source 151 such as a battery. In a preferred embodiment, the neuroregulator further comprises a power source, wherein the power source 151 is a rechargeable battery. In some embodiments, the power source 151 can provide power to the implanted neuroregulator 104 when the external charger 101 is not connected. In other embodiments, the external charger 101 also can be configured to provide for periodic recharging of the internal power source 151 of the neuroregulator 104. In an alternative embodiment, however, the neuroregulator 104 can entirely depend upon power received from an external source. For example, the external charger 101 can transmit power to the neuroregulator 104 via the RF link (e.g., between coils 102, 105).

In some embodiments, the neuroregulator 104 initiates the generation and transmission of therapy signals to the lead assemblies 106, 106a. In an embodiment, the neuroregulator 104 initiates therapy when powered by the internal battery 151. In other embodiments, however, the external charger 101 triggers the neuroregulator 104 to begin generating therapy signals. After receiving initiation signals from the external charger 101, the neuroregulator 104 generates the therapy signals (e.g., pacing signals) and transmits the therapy signals to the lead assemblies 106, 106a.

In other embodiments, the external charger 101 also can provide the instructions according to which the therapy signals are generated (e.g., pulse-width, amplitude, and other such parameters). In a preferred embodiment, the external charger 101 includes memory in which several predetermined programs/therapy schedules can be stored for transmission to the neuroregulator 104. The external charger 101 also can enable a user to select a program/therapy schedule stored in memory for transmission to the neuroregulator 104. In another embodiment, the external charger 101 can provide treatment instructions with each initiation signal.

Typically, each of the programs/therapy schedules stored on the external charger 101 can be adjusted by a physician to suit the individual needs of the patient. For example, a computing device (e.g., a notebook computer, a personal computer, etc.) 100 can be communicatively connected to the external charger 101. With such a connection established, a physician can use the computing device 107 to program therapies into the external charger 101 for either storage or transmission to the neuroregulator 104.

The neuroregulator 104 also may include memory in which treatment instructions and/or patient data can be stored. For example, the neuroregulator 104 can store therapy programs indicating what therapy should be delivered to the patient. The neuroregulator 104 also can store patient data indicating how the patient utilized the therapy system and/or reacted to the delivered therapy.

Referring to FIG. 1, the circuitry 170 of the external mobile charger 101 can be connected to an external coil 102. The coil 102 communicates with a similar coil 105 implanted within the patient and connected to the circuitry 150 of the impulse generator 104. Communication between the external mobile charger 101 and the impulse generator 104 includes transmission of pacing parameters and other signals as will be described.

Having been programmed by signals from the external mobile charger 101, the impulse generator 104 generates upregulating signals or downregulating signals to the leads 106, 106a. As will be described, the external mobile charger 101 may have additional functions in that it may provide for periodic recharging of batteries within the impulse generator 104, and also allow record keeping and monitoring.

While an implantable (rechargeable) power source for the impulse generator 104 is preferred, an alternative design could utilize an external source of power, the power being transmitted to an implanted module via the RF link (i.e., between coils 102, 105). In this alternative configuration, while powered externally, the source of the specific blocking signals could originate either in the external power source unit, or in the implanted module.

The electronic energization package may, if desired, be primarily external to the body. An RF power device can provide the necessary energy level. The implanted components could be limited to the lead/electrode assembly, a coil and a DC rectifier. With such an arrangement, pulses programmed with the desired parameters are transmitted through the skin with an RF carrier, and the signal is thereafter rectified to regenerate a pulsed signal for application as the stimulus to the vagus nerve to modulate vagal activity. This would virtually eliminate the need for battery changes.

However, the external transmitter must be carried on the person of the patient, which is inconvenient. Also, detection is more difficult with a simple rectification system, and greater power is required for activation than if the system were totally implanted. In any event, a totally implanted system is expected to exhibit a relatively long service lifetime, amounting potentially to several years, because of the relatively small power requirements for most treatment applications. Also, as noted earlier herein, it is possible, although considerably less desirable, to employ an external impulse generator with leads extending percutaneously to the implanted nerve electrode set. The major problem encountered with the latter technique is the potential for infection. Its advantage is that the patient can undergo a relatively simple procedure to allow short term tests to determine whether the condition associated with excess weight of this particular patient is amenable to successful treatment. If it is, a more permanent implant may be provided.

According to an embodiment of the present invention, an apparatus is disclosed for applying an electrical signal to an internal anatomical feature of a patient. The apparatus includes at least one electrode for implantation within the patient and placement at the anatomical feature (e.g., a nerve) for applying the signal to the feature upon application of the signal to the electrode. An implantable component is placed in the patient's body beneath a skin layer and having an implanted circuit connected to the electrode. The implanted circuit includes an implanted communication antenna. An external component has an external circuit with an external communication antenna for placement above the skin and adapted to be electrically coupled to the implanted antenna across the skin through radiofrequency transmission. The external circuit has a plurality of user interfaces including an information interface for providing information to a user and an input interface for receiving inputs from the user.

Figure 2:
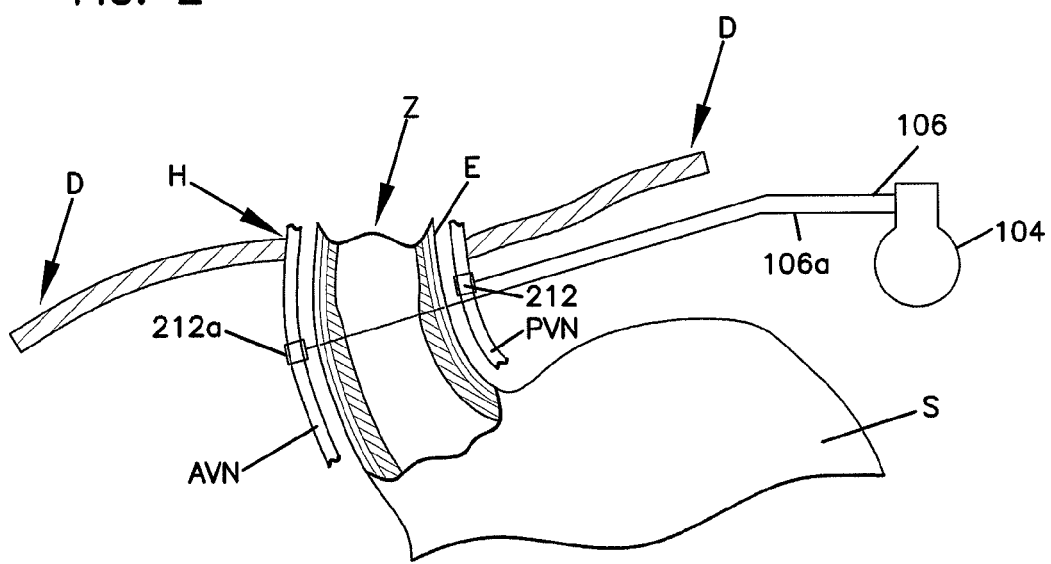
FIG. 2 is a schematic representation of an exemplary impulse generator and leads.

With reference to FIG. 2, a device is shown for application of a signal to a nerve. A stomach S is shown schematically for the purpose of facilitating an understanding of applying a vagal nerve modulating signal. The esophagus E passes through the diaphragm D at an opening or hiatus H. In the region where the esophagus E passes through the diaphragm D, trunks of the vagal nerve (illustrated as the anterior vagus nerve AVN and posterior vagus nerve PVN) are disposed on opposite sides of the esophagus E. It will be appreciated that the precise location of the anterior and posterior vagus nerves AVN, PVN relative to one another and to the esophagus E are subject to a wide degree of variation within a patient population. However, for most patients, the anterior and posterior vagus nerves AVN, PVN are in close proximity to the esophagus E at the hiatus H where the esophagus E passes through the diaphragm D.

The anterior and posterior vagus nerves AVN, PVN divide into a plurality of trunks that innervate the stomach directly and via the enteric nervous system and may include portions of the nerves which may proceed to other organs such as the pancreas, gallbladder and intestines. Commonly, the anterior and posterior vagus nerves AVN, PVN are still in close proximity to the esophagus E and stomach (and not yet extensively branched out) at the region of the junction of the esophagus E and stomach S. In the region of the hiatus H, there is a transition from esophageal tissue to gastric tissue. This region is referred to as the Z-line (labeled "Z" in the Figure). Above the Z-line, the tissue of the esophagus is thin and fragile. Below the Z-line, the tissue of the esophagus E and stomach S are substantially thickened and more vascular. Within a patient population, the Z-line is in the general region of the lower esophageal sphincter. This location may be slightly above, slightly below or at the location of the hiatus H.

Figure 3:
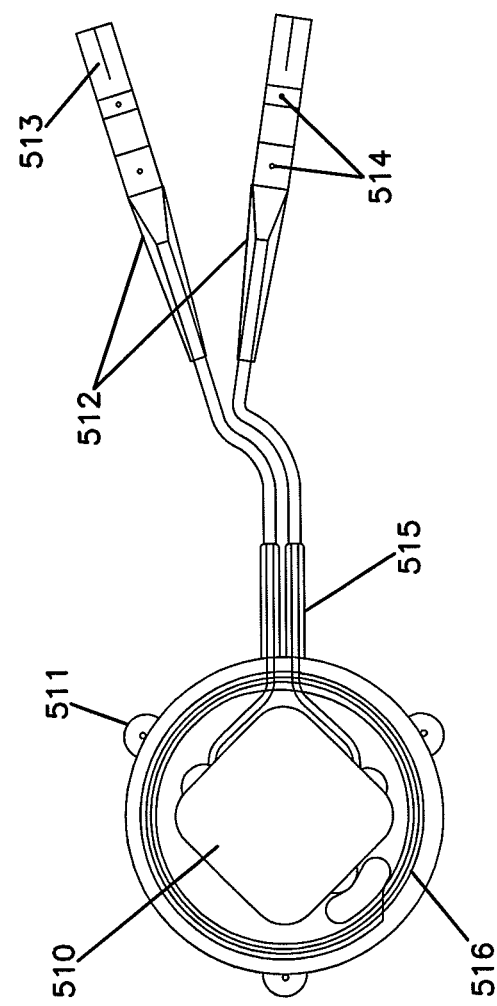
FIG. 3 illustrates a schematic representative of another exemplary embodiment comprising an implantable component comprising an electronic assembly 510 ("hybrid circuit") and a receiving coil 516; standard connectors 512 (e.g. IS-1 connectors) for attachment to electrode leads. Two leads are connected to the IS-1 connectors for connection to the implanted circuit. Both have a tip electrode for placement on a nerve. The patient receives an external controller comprising an antenna connected to control circuitry. The external control unit can be programmed for various signal parameters including options for frequency selection, pulse amplitude and duty cycle.

Another embodiment of a device useful in treating a condition associated with impaired blood pressure regulation as described herein is shown in FIG. 3. With reference to FIG. 3, a device comprises an implantable component comprising an electronic assembly 510 ("hybrid circuit") and a receiving coil 516; standard connectors 512 (e.g. IS-1 connectors) for attachment to electrode leads. The implantable component may also comprise a memory and/or a microprocessor that may be configured to deliver an electrical signal having specific parameters including frequency, voltage, amplitude, pulse width, and timing. Two leads are connected to the IS-1 connectors for connection to the implanted circuit. Both have a an electrode for placement on a nerve. Set screws are shown in 514 and allow for adjustment of the placement of the electrodes. In some embodiments, a marker 513 to indicate the posterior or anterior lead is provided. Suture tabs 511 are provided to provide for implantation at a suitable site. In some embodiments, strain relief 515 is provided. The patient receives an external controller comprising an antenna connected to control circuitry. The external control unit can be programmed for various signal parameters including options for frequency selection, pulse amplitude and duty cycle.

In an embodiment, the nerves AVN, PVN are indirectly stimulated by passing electrical signals through the tissue surrounding the nerves. In some embodiments, the electrodes are bipolar pairs (ie. alternating anode and cathode electrodes). In some embodiments, a plurality of electrodes may be placed overlying the anterior and/or posterior vagus nerves AVN, PVN. As a result, energizing the plurality of electrodes will result in application of a signal to the anterior and posterior vagus nerves AVN, PVN and/or their branches. In some therapeutic applications, some of the electrodes may be connected to a blocking electrical signal source (with a blocking frequency and other parameters as described below). Of course, only a single array of electrodes could be used with all electrodes connected to a blocking or a downregulating signal.

The electrical connection of the electrodes to an impulse generator may be as previously described by having a lead (eg. 106,106a) connecting the electrodes directly to an implantable impulse generator (eg. 104). Alternatively, and as previously described, electrodes may be connected to an implanted antenna for receiving a signal to energize the electrodes.

Two paired electrodes may connect to a pulse generator for bi-polar signals. In other embodiments, a portion of the vagus nerve VN is dissected away from the esophagus E. An electrode is placed between the nerve VN and the esophagus E. Another electrode is placed overlying the vagus nerve VN on a side of the nerve opposite the first electrode and with electrodes axially aligned (i.e., directly across from one another). Not shown for ease of illustration, the electrodes may be carried on a common carrier (e.g., a PTFE or silicone cuff) surrounding the nerve VN. Other possible placements of electrodes are described herein US 2005/0131485 published Jun. 16, 2005, which patent publication is hereby incorporated by reference.

While any of the foregoing electrodes could be flat metal pads (e.g., platinum), the electrodes can be configured for various purposes. In an embodiment, an electrode is carried on a patch. In other embodiments, the electrode is segmented into two portions both connected to a common lead and both connected to a common patch. In some embodiments, each electrode is connected to a lead and placed to deliver a therapy from one electrode to another. A flexible patch permits articulation of the portions of the electrodes to relieve stresses on the nerve VN.

Neuroregulator (Impulse Generator)

The neuroregulator (impulse generator) generates electrical signals in the form of electrical impulses according to a programmed regimen. In embodiments, a downregulating or blocking signal is applied as described herein. The impulse generator utilizes a microprocessor and other electrical and electronic components, and communicates with an external programmer and/or monitor by asynchronous serial communication for controlling or indicating states of the device. Passwords, handshakes and parity checks are employed for data integrity. The impulse generator also includes means for conserving energy, which is important in any battery operated device and especially so where the device is implanted for medical treatment of a disorder, and means for providing various safety functions such as preventing accidental reset of the device.

Features may be incorporated into the impulse generator for purposes of the safety and comfort of the patient. In some embodiments, the patient's comfort would be enhanced by ramping the application of the signal up. The device may also have a clamping circuit to limit the maximum voltage (20 volts for example) deliverable to the vagus nerve, to prevent nerve damage. An additional safety function may be provided by implementing the device to cease signal application in response to manual deactivation through techniques and means similar to those described above. In this way, the patient may interrupt the signal application if for any reason it suddenly becomes intolerable.

The intermittent aspect of the blocking resides in applying the signal according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective.

Impulse generators, one supplying the right vagus and the other the left vagus to provide the bilateral upregulation or downregulation may be used. Use of implanted impulse generators for performing the method of the invention is preferred, but treatment may conceivably be administered using external equipment on an outpatient basis, albeit only somewhat less confining than complete hospitalization. Implantation of one or more impulse generators, of course, allows the patient to be completely ambulatory, so that normal daily routine activities including on the job performance is unaffected.

In some embodiments, signals can also be applied at a portion of the nervous system remote from the vagus nerve at the subdiaphragmatic location such as at or near the cardiac notch. Signals can also be applied at other sympathetic nerves and/or baroreceptors in combination with application of a signal to the vagus nerve such as a down regulating signal. Here, at least one impulse generator is implanted together with one or more electrodes subsequently operatively coupled to the impulse generator via leads for generating and applying the electrical signal internally to a portion of the patient's nervous system to provide indirect blocking, down regulation, or up regulation of the vagus nerve or other nerves or receptors in the vicinity of the desired location.

In some embodiments, the electrical signal is applied intermittently to downregulate the vagus nerve at a location below vagal innervation of the cardiac region without application of any other downregulating and/or upregulating signal on the vagus nerve or other nerves.

It is surprising that downregulation of the vagus nerve at a location below the innervation of the cardiac region, e.g. subdiaphragamatically would be effective to decrease blood pressure and heart rate. In some cases, the blood pressure is decreased to or near the normal range. In a typical situation of high blood pressure, the vagus nerve operates to slow the heart rate to assist in decreasing the blood pressure and thus, it is surprising that downregulating and/or blocking of the vagus nerve would be effective to lower heart rate and blood pressure. In addition, clinical benefits may include lowering the blood pressure early in treatment and with minimal adverse clinical effects. Little or no side effects have been observed with this treatment in contrast to side effects often associated with drug treatment. Patients without hypertension or without prehypertension show no effect on blood pressure during electrical signal treatment.

In other embodiments, to decrease heart rate and/or blood pressure, a down regulating signal may be applied to the vagus nerve at a location below the vagal innervation of the heart and another signal applied elsewhere such as an up regulating signal applied at the right vagus nerve at SA node or a down regulating signal applied to a sympathetic nerve innervating the heart. In other cases, to decrease blood pressure, a down regulating signal may be applied to the vagus nerve at a location below the vagal innervation of the heart and another signal applied elsewhere such as an up regulating signal applied at the right vagus nerve at SA node, an upregulating signal to the baroreceptors, or a downregulating signal to the sympathetic nerves innervating the heart.

Alternatively, the electrical signal may be applied non-invasively to a portion of the patient's nervous system for indirect application of the vagus nerve at a sub-diaphragmatic location. The electrical signal may be applied to an electrode positioned intravascularly.

The impulse generator may be programmed with a programming wand and a personal computer using suitable programming software developed according to the programming needs and signal parameters which have been described herein. The intention, of course, is to permit noninvasive communication with the electronics package after the latter is implanted, for both monitoring and programming functions. Beyond the essential functions, the programming software should be structured to provide straightforward, menu-driven operation, HELP functions, prompts, and messages to facilitate simple and rapid programming while keeping the user fully informed of everything occurring at each step of a sequence. Programming capabilities should include capability to modify the electronics package's adjustable parameters, to test device diagnostics, and to store and retrieve telemetered data. It is desirable that when the implanted unit is interrogated, the present state of the adjustable parameters is displayed on the PC monitor so that the programmer may then conveniently change any or all of those parameters at the same time; and, if a particular parameter is selected for change, all permissible values for that parameter are displayed so that the programmer may select an appropriate desired value for entry into the impulse generator.

Adjustable parameters include frequency, pulse width, on and off times, current, and ON/OFF ramps. One or more of the parameters are selected to decrease heart rate and/or blood pressure without adverse clinical effects.

The frequency is selected to provide at least a partial decrease in activity of the nerve. In some embodiments, the neuroregulator is configured to deliver a signal of about 200 Hz to 25 kHz, 200 Hz to about 15 kHz, 200 Hz to about 10 kHz, 200 to 5000 Hz, 250 to 5000 Hz, 300 to 5000 Hz, 400 to 5000 Hz, 500 to 5000 Hz, 200 to 2500 Hz, 300 to 2500 Hz, 400 to 2500 Hz, 500 to 2500 Hz, and any frequencies in between 200 Hz to 25 kHz or combinations thereof.

The on times are selected to provide at least a partial decrease in nerve activity. In embodiments, the neuroregulator is configured to deliver on times of from 30 seconds to 30 minutes, 30 seconds to 20 minutes, 30 seconds to 10 minutes, 30 seconds to 5 minutes, 30 sec to 3 minutes, 30 seconds to 2 minutes, or 30 seconds to 1 minute or combinations thereof. The off times are selected to allow at least partial recovery of the nerve activity. In embodiments, the neuroregulator is configured to deliver off times of from 30 seconds to 30 minutes, 30 seconds to 20 minutes, 30 seconds to 10 minutes, 30 seconds to 5 minutes, 30 sec to 3 minutes, 30 seconds to 2 minutes, or 30 seconds to 1 minute or combinations thereof. I In other embodiments other on times and off time may be utilized as appropriate for the patient's condition and responsiveness to treatment. For example, the on times may be 30 minutes or longer followed by an off time of at least 24 hours or longer. A specific embodiment includes one or more therapy on periods of up to 30 minutes with intervening therapy off periods for up to 7 days or longer.

In embodiments, the current and/or voltage are adjusted based on safety and efficacy of treatment for the patient. In some embodiments, the signal amplitude can range from 0.5 mA to about 18 mA including amplitudes in between that differ by 0.25 mA or other larger or smaller increments, adjusted up or down based on patient response. Voltages can range from 0.25 volts up to 20 volts or voltage in between that differ by 0.25 volts, or other larger or smaller increments, adjusted up or down based on patient response.

The treatment time can be an entire 24 hour period, 18 to 24 hours, 16 to 24 hours, 12 to 24 hours, and 8 to 24 hours, 6 to 24 hours, 4 to 24 hours or other intervals that match the treatment needs and/or activities of daily living of the patient or combinations thereof. Treatment time may be varied depending on whether the patient experiences a drop in blood pressure while sleeping. (Pickering et al, N. Eng. J. Med. 354:22 (2002)). Some patients who have hypertension have a blood pressure of greater than or equal to 135/85 mm Hg while they are awake and greater than or equal to 120/75 mm Hg when they are asleep. For those patients, the treatment would not be administered during some of the sleeping hours of the patient. However, in most cases, treatment would resume as early as 4 am in order to minimize the early morning spike in blood pressure that can lead to heart attack or stroke. (Pickering et al, cited supra) In other cases, for those patients who do not experience a drop in blood pressure while they are sleeping, treatment may be administered for a full 24 hour period.

Other desirable features of appropriate software and related electronics would include the capability to store and retrieve historical data, including patient code, device serial number, number of hours of battery operation, number of hours of output, and number of magnetic activations (indicating patient intercession) for display on a screen with information showing date and time of the last one or more activations.

Diagnostic testing should be implemented to verify proper operation of the device, and to indicate the existence of problems such as with communication, the battery, or the lead/electrode impedance. A low battery reading, for example, would be indicative of imminent end of life of the battery and need for implantation of a new device. However, battery life should considerably exceed that of other implantable medical devices, such as cardiac pacemakers, because of the relatively less frequent need for activation of the pulse generator of the present invention. In any event, the nerve electrodes are capable of indefinite use absent indication of a problem with them observed on the diagnostics testing.

The device may utilize circadian or other programming as well, so that activation occurs automatically at normal mealtimes for this patient. This may be in addition to the provision for the manual, periodic between meal, and sensing-triggered activation as described above herein.

The impulse generator may also be activated manually by the patient by any of various means by appropriate implementation of the device. These techniques include the patient's use of an external magnet, or of an external RF signal generator, or tapping on the surface overlying the impulse generator, to activate the impulse generator and thereby cause the application of the desired modulating signal to the electrodes. Another form of treatment may be implemented by programming the impulse generator to periodically deliver the vagal activity modulation productive of glycemic control at programmed intervals.

C. Methods

The disclosure provides methods of regulating heart rate and/or blood pressure. In some embodiments, a method comprises: applying an intermittent electrical signal to a target nerve at a site with said electrical signal selected to downregulate and/or upregulate neural activity on the nerve and with neural activity at least partially restoring upon discontinuance of said signal. In some embodiments, the methods further comprise administering a composition to the subject comprising an effective amount of an agent that controls blood pressure or treats congestive heart failure. In some embodiments, the electrical signal is applied to the nerve by implanting a device or using a system as described herein.

In some embodiments, a method of treating hypertension or pre-hypertension in a subject comprises applying an intermittent neural conduction signal to a target nerve of the subject having hypertension at a site on the vagus nerve, with said neural conduction signal selected to down-regulate neural activity on the nerve and to at least partially restore neural activity on the nerve upon discontinuance of said signal. In other embodiments, the nerve conduction signal is applied continuously during the time of treatment. In embodiments, the treatment is applied without any other upregulating or downregulating signal on the vagus nerve or other nerves. In embodiments, the treatment and/or signal characteristic are selected so that no other adverse clinical effects occur.

In some embodiments, a method of treating hypotension in a subject comprises applying an intermittent neural conduction signal to a target nerve of the subject having hypotension at a site on the vagus nerve, with said neural conduction signal selected to up-regulate neural activity on the nerve and to at least partially restore neural activity on the nerve upon discontinuance of said signal. In other embodiments, the nerve conduction signal is applied continuously during the time of treatment.

In other embodiments, methods include a treatment for hypertension, congestive heart failure, pre-hypertension, or other conditions having hypertension as a component, comprising selecting a drug for treating hypertension, congestive heart failure, or other condition for a patient where effective dosages for treating such conditions for such a patient are associated with disagreeable side effects or impaired blood pressure control; and treating the patient with a concurrent treatment comprising: a) applying an intermittent neural block to a target nerve of the patient at multiple times per day and over multiple days with the block selected to downregulate afferent and/or efferent neural activity on the nerve and with neural activity at least partially restoring upon discontinuance of said block; and b) administering said drug to the patient.

In other embodiments, a down regulating signal may be combined with an up regulating signal at another nerve or another location. For example, for treatment of hypertension, a down regulating signal may be applied to the vagus nerve at a subdiaphragmatic location and up regulating signal applied to the baroreceptors or to the tissue surrounding the baroreceptors. In another case, a down regulating signal can be applied to the vagus nerve at a subdiaphragmatic location and an up regulating signal applied to the vagus nerve at the carotid sinus or aortic arch. Down regulating signals may also be applied to nerves associated with the sympathetic nerve system innervating the heart.

Signal Application

In one aspect of the disclosure a reversible intermittent modulating signal is applied to a target nerve in order to downregulate and/or upregulate neural activity on the nerve. In other embodiments a signal is applied to a target nerve to upregulate or downregulate neural activity continuously during the treatment time. In embodiments, the target nerve is the vagus nerve.

In embodiments of the methods described herein a neural conduction block is applied to a target nerve at a site with said neural conduction block selected to down-regulate neural activity on the nerve and with neural activity at least partially restoring upon discontinuance of said signal.

In some embodiments, said modulating signal comprises applying an electrical signal. The signal is selected to down regulate or up regulate neural activity and allow for at least partial restoration of the neural activity upon discontinuance of the signal. An impulse generator, as described above, can be employed to regulate the application of the signal in order to alter the characteristic of the signal to provide a reversible intermittent signal. The characteristics of the signal include location of the signal, frequency of the signal, amplitude of the signal, voltage of the signal, pulse width of the signal, ramp-up and ramp-down characteristics and the administration cycle of the signal. In some embodiments, the signal characteristics are selected to provide for improved heart rate and/or blood pressure.

Figure 4:
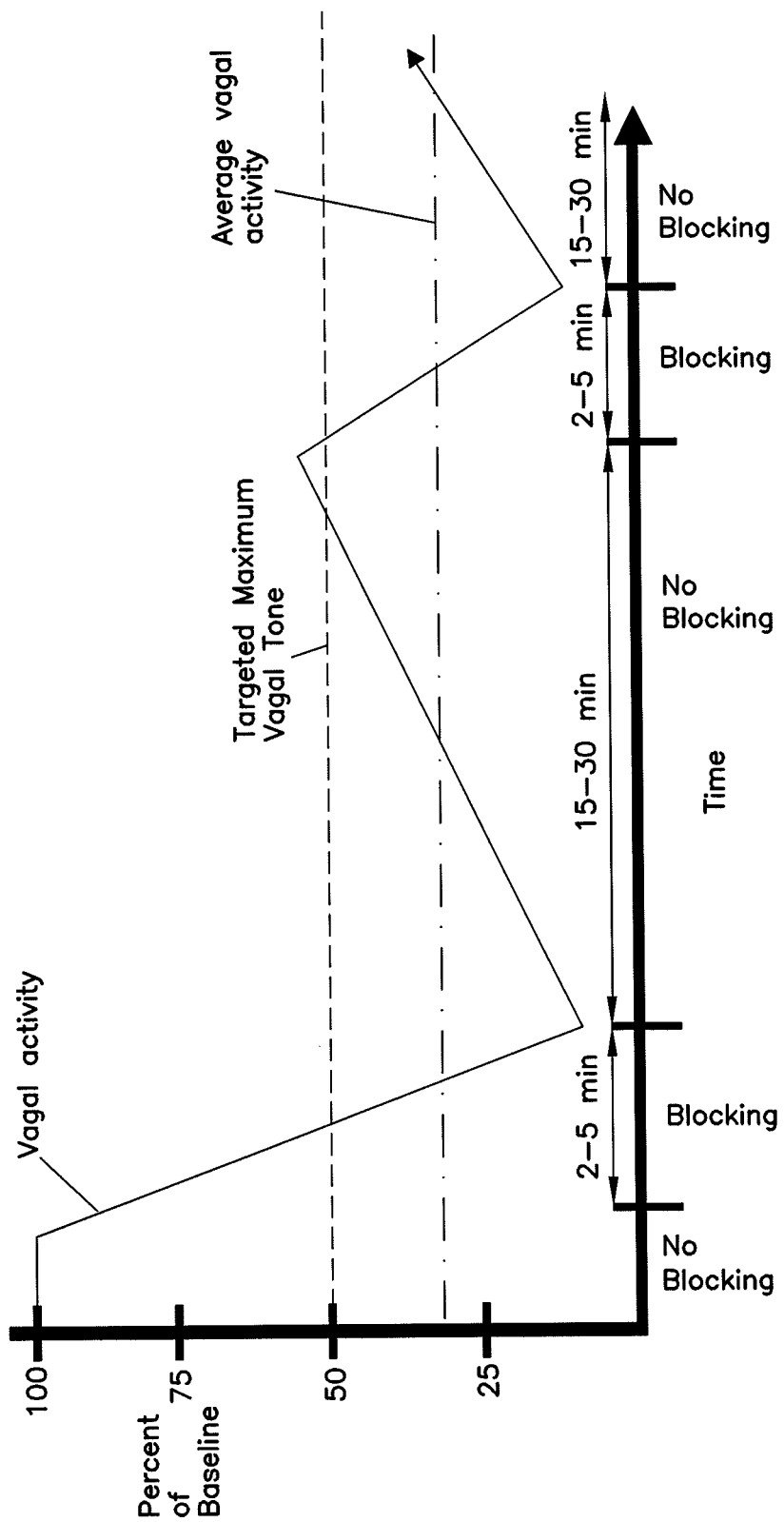
FIG. 4 shows recovery of the vagal nerve after application of blocking signal.

In some embodiments, electrodes applied to a target nerve are energized with an intermittent blocking or down regulating signal. The signal is applied for a limited time (e.g., 5 minutes). The speed of neural activity recovery varies from subject to subject. However, 20 minutes is a reasonable example of the time needed to recover to baseline. After recovery, application of a blocking signal again down-regulates neural activity which can then at least partially recover after cessation of the signal. Renewed application of the signal can be applied before full recovery. For example, after a limited time period (e.g., 10 minutes) blocking can be renewed resulting in average neural activity not exceeding a level significantly reduced when compared to baseline. In some embodiments, the electrical signal is applied intermittently in a cycle including an on time of application of the signal followed by an off time during which the signal is not applied to the nerve, wherein the on and off times are applied multiple times per day over multiple days Recognition of recovery of neural activity, such as vagal activity, permits a treatment therapy and apparatus with enhanced control and enhanced treatment options. FIG. 4 illustrates vagal activity over time in response to application of a blocking signal as described above and further illustrates recovery of vagal activity following cessation of the blocking signal. It will be appreciated that the graph of FIG. 4 is illustrative only. It is expected there will be significant patient-to-patient variability. For example, some patients' responses to a blocking signal may not be as dramatic as illustrated. Others may experience recovery slopes steeper or shallower than illustrated. Also, vagal activity in some subjects may remain flat at a reduced level before increasing toward baseline activity. However, based on the afore-mentioned animal experiments, FIG. 4 is believed to be a fair presentation of a physiologic response to blocking.

In FIG. 4, vagal activity is illustrated as a percent of baseline (i.e., vagal activity without the treatment of the present invention). Vagal activity can be measured in any number of ways. For example, quantities of pancreatic exocrine secretion produced per unit time are an indirect measurement of such activity. Also, activity can be measured directly by monitoring electrodes on or near the vagus. Such activity can also be ascertained qualitatively (e.g., by a patient's sensation of bloated feelings or normalcy of gastrointestinal motility).

In FIG. 4, the vertical axis is a hypothetical patient's vagal activity as a percent of the patient's baseline activity (which varies from patient to patient). The horizontal axis represents the passage of time and presents illustrative intervals when the patient is either receiving a blocking signal as described or the blocking signal is turned off (labeled "No Blocking"). As shown in FIG. 4, during a short period of receiving the blocking signal, the vagal activity drops dramatically (in the example shown, to about 10% of baseline activity). After cessation of the blocking signal, the vagal activity begins to rise toward baseline (the slope of the rise will vary from patient to patient). The vagal activity can be permitted to return to baseline or, as illustrated in FIG. 4, the blocking signal can be re-instituted when the vagal activity is still reduced. In FIG. 4, the blocking signal begins when the vagal activity increases to about 50% of baseline. As a consequence, the average vagal activity is reduced to about 30% of the baseline activity. It will be appreciated that by varying the blocking time duration and the "no blocking" time duration, the average vagal activity can be greatly varied.

The signal may be intermittent or continuous. The preferred nerve conduction block is an electronic block created by a signal at the vagus by an electrode controlled by the implantable impulse generator (such as impulse generator 104 or an external controller). The nerve conduction block can be any reversible block. For example, ultrasound, alteration in temperature, or drug blocks can be used. An electronic block may be a Peltier solid-state device which cools in response to a current and may be electrically controlled to regulate cooling. Piezo-electric devices can be used to apply a mechanical energy to the nerve(s) to modulate activity. Drug blocks may include a pump-controlled subcutaneous drug delivery.

With such an electrode conduction block, the block parameters (signal type and timing) can be altered by impulse regulator and can be coordinated with the upregulating signals. For example, the nerve conduction block parameters for muscles are disclosed in Solomonow, et al., "Control of Muscle Contractile Force through Indirect High-Frequency Stimulation", Am. J. of Physical Medicine, Vol. 62, No. 2, pp. 71-82 (1983). In some embodiments, the nerve conduction block is applied with electrical signal selected to block the entire cross-section of the nerve (e.g., both afferent, efferent, myelinated and nomnyelinated fibers) at the site of applying the blocking signal (as opposed to selected sub-groups of nerve fibers or just efferent and not afferent or vice versa) and, more preferably, has a frequency selected to exceed the 200 Hz threshold frequency. Further, more preferred parameters are a frequency of 5000 Hz (with other parameters, as non-limiting examples, being amplitude of 6 mA, pulse width of 0.09 msec, and duty cycle of 5 minutes on and 5 minutes off). As will be more fully described, the present invention gives a physician great latitude in selected pacing and blocking parameters for individual patients.

In embodiments, the signal parameters provide for a decrease in heart rate and/or blood pressure, preferably without affecting other cardiac functions. The frequency is selected to provide at least a partial decrease in activity of the nerve. In some embodiments, the neuroregulator is configured to deliver a signal of about 200 Hz to 25 kHz, 200 Hz to about 15 kHz, 200 Hz to about 10 kHz, 200 to 5000 Hz, 250 to 5000 Hz, 300 to 5000 Hz, 400 to 5000 Hz, 500 to 5000 Hz, 200 to 2500 Hz, 300 to 2500 Hz, 400 to 2500 Hz, 500 to 2500 Hz, and any frequencies in between 200 Hz to 25 kHz or combinations thereof.

The on times are selected to provide at least a partial decrease in nerve activity. In embodiments, the neuroregulator is configured to deliver on times of from 30 seconds to 30 minutes, 30 seconds to 20 minutes, 30 seconds to 10 minutes, 30 seconds to 5 minutes, 30 sec to 3 minutes, 30 seconds to 2 minutes, or 30 seconds to 1 minute or combinations thereof. The off times are selected to allow at least partial recovery of the nerve activity. In embodiments, the neuroregulator is configured to deliver off times of from 30 seconds to 30 minutes, 30 seconds to 20 minutes, 30 seconds to 10 minutes, 30 seconds to 5 minutes, 30 sec to 3 minutes, 30 seconds to 2 minutes, or 30 seconds to 1 minute or combinations thereof.

In other embodiments other on times and off time may be utilized as appropriate for the patient's condition and responsiveness to treatment. For example, the on times may be 30 minutes or longer followed by an off time of at least 30 minutes, or an on time of at least 30 minutes followed by an off time of 24 hours or longer. A specific embodiment includes one or more therapy on periods of at least 30 minutes with intervening therapy off periods for up to 7 days or longer.

In embodiments, the current and/or voltage are adjusted based on safety and efficacy of treatment for the patient. In some embodiments, the signal amplitude can range from 0.5 mA to about 18 mA including amplitudes in between that differ by 0.25 mA, or other larger or smaller increments, adjusted up or down based on patient response. Voltages can range from 0.25 volts up to 20 volts or voltages in between that differ by 0.25 volts, or other larger or smaller increments, adjusted up or down based on patient response.

The treatment time can be an entire 24 hour period, 18 to 24 hours, 16 to 24 hours, 12 to 24 hours, and 8 to 24 hours, 6 to 24 hours, 4 to 24 hours or other intervals that match the treatment needs and/or activities of daily living of the patient or combinations thereof. Treatment time may be varied depending on whether the patient experiences a drop in blood pressure while sleeping. (Pickering et al, N. Eng. J. Med. 354:22 (2002)). Some patients who have hypertension have a blood pressure of greater than or equal to 135/85 mm Hg while they are awake and greater than or equal to 120/75 mm Hg when they are asleep. For those patients, the treatment would not be administered during some of the sleeping hours of the patient. However, in most cases, treatment would resume as early as 4 am in order to minimize the early morning spike in blood pressure that can lead to heart attack or stroke. (Pickering et al, cited supra) In other cases, for those patients who do not experience a drop in blood pressure while they are sleeping, treatment may be administered for a full 24 hour period.

In embodiments, a down regulating signal is applied to the vagus nerve at a location below the vagal innervation of the heart. In other embodiments, a down regulating signal is applied to the vagus nerve at a location below the vagal innervation of the heart and a down regulating signal is applied to a sympathetic nerve innervating the heart.

In embodiments of the methods described herein a signal is applied to a target nerve at a site with said signal selected to up-regulate neural activity on the nerve and with neural activity at least partially restoring upon discontinuance of said signal. In some embodiments, an upregulating signal may be applied in combination with a down regulating signal in order to improve heart rate and/or blood pressure.

The signal is selected to upregulate neural activity and allow for restoration of the neural activity upon discontinuance of the signal. To decrease heart rate and blood pressure, an upregulating signal may be applied at the right vagus nerve near the SA node of the heart or an upregulating signal may be applied to the baroreceptors. An impulse generator, as described above, is employed to regulate the application of the signal in order to alter the characteristic of the signal to provide a reversible intermittent signal. The characteristics of the signal include frequency of the signal, location of the signal, and the administration cycle of the signal.

In some embodiments, electrodes applied to a target nerve are energized with an up regulating signal. The signal is applied for a limited time (e.g., 5 minutes). The speed of neural activity recovery varies from subject to subject. However, 20 minutes is a reasonable example of the time needed to recover to baseline. After recovery, application of an up signal again up-regulates neural activity which can then recover after cessation of the signal. Renewed application of the signal can be applied before full recovery. For example, after a limited time period (e.g., 10 minutes) upregulating signal can be renewed. Frequencies for upregulation include frequencies of about 1 to 200 Hz, 1 to 150 Hz, 1 to 100 Hz, 1 to 75 Hz, 1 to 50 Hz, 1 to 25 Hz, or combinations thereof.

In some embodiments, an upregulating signal may be applied in combination with a down regulating signal in order to improve heart rate and/or blood pressure. The upregulating and down regulating signals may be applied to different nerves at the same time, applied to the same nerve at different times, or applied to different nerves at different times. For example, a downregulating signal may be applied during the day when blood pressure tends to be higher, followed by a stimulatory signal while sleeping.

Location of Signal Application

Modulation of neural activity can be achieved by upregulating and/or down regulating neural activity of a target nerve.

In some embodiments, electrodes can be positioned at a number of different sites and locations on or near a target nerve. Target nerves include the vagus nerve, glossopharyngeal nerve, cardiac sinus nerve, and sympathetic nerves innervating the heart. In some embodiments, the electrode is positioned to apply an electrical signal to the nerve at a location near or distal to the diaphragm of the subject. Electrodes may be positioned on different nerves to apply a down regulating signal as opposed to an up regulating signal. For example, a down regulating signal can be applied on the vagus nerve and an up regulating signal applied to the baroreceptors. In other cases, a down regulating signal can be applied on the vagus nerve at a location below the vagal innervation of the heart and a down regulating signal applied to sympathetic nerves innervating the heart.

In some embodiments, the electrode is positioned to apply a signal to a branch or trunk of the vagus nerve. In other embodiments, the electrode is positioned to apply a signal to an anterior trunk, posterior trunk or both. In some embodiments, the electrode is positioned below vagal innervation of the heart such as at a subdiaphragmatic location.

In an embodiment, a blocking electrode is placed high on the vagus relative to the GI tract innervation (e.g., just below the diaphragm), or the sole blocking electrode could be placed lower (e.g., just proximal to pancreo/biliary innervation. Blocking of the entire vagus as described above can be used to down-regulate the vagus for various benefits including treating a condition associated with impaired heart rate and/or blood pressure. In other embodiments, alternative designs for placing electrodes on or near the vagus nerve in a region of the esophagus E either above or below the diaphragm are provided.

Two paired electrodes may connect to a pulse generator for bi-polar signals. In other embodiments, a portion of the vagus nerve VN is dissected away from the esophagus E. An electrode is placed between the nerve VN and the esophagus E. The electrode is placed overlying the vagus nerve VN on a side of the nerve opposite electrode and with electrodes axially aligned (i.e., directly across from one another). Other possible placements of electrodes are described herein US 2005/0131485 published Jun. 16, 2005, which patent publication is hereby incorporated by reference.

Signal Frequency and Timing

In some embodiments, a downregulating signal has a frequency of at least 200 Hz and up to 25 kHz or any frequency in between. In other embodiments, the signal is applied at a frequency of about 500 to 5000 Hz. Applicant has determined a most preferred blocking signal has a frequency of 2000 Hz to 5,000 Hz or greater applied by two or more bi-polar electrodes. Such a signal has a preferred pulse width of 100 micro-seconds (associated with a frequency of 5,000 Hz). It is believed this frequency and pulse width best provide neural recovery from blocking and avoid repolarization of the nerve by avoiding periods of no signal in the pulse cycle. A short "off" time in the pulse cycle (e.g., between cycles or within a cycle) could be acceptable as long as it is short enough to avoid nerve repolarization. The waveform may be a square or sinusoidal waveform, monophasic or biphasic, or other shape. The higher frequencies of 5,000 Hz or more have been found, in porcine studies, to result in more consistent neural conduction block. Preferably the signal is bi-polar, biphasic delivered to two or more electrodes on a nerve.

In some embodiments, a signal amplitude of 0.5 to 8 mA is adequate for blocking. Other amplitudes may suffice as described herein, such as 0.5 mA to 18 mA. Other signal attributes can be varied to reduce the likelihood of accommodation by the nerve or an organ. These include altering the power, waveform or pulse width.

Upregulating signals comprise signals of a frequency of less than 200 Hz, more preferably 10 to 150 Hz, and more preferably 10 to 50 Hz.

Selection of a signal that upregulates and/or downregulates neural activity and/or allows for recovery of neural activity can involve selecting signal type and timing of the application of the signal. For example, with an electrode conduction block, the block parameters (signal type and timing) can be altered by the impulse generator and can be coordinated with the stimulating signals. The precise signal to achieve blocking may vary from patient to patient and nerve site. The precise parameters can be individually tuned to achieve neural transmission blocking at the blocking site.

In some embodiments, the signal has a duty cycle including an ON time during which the signal is applied to the nerve followed by an OFF time during which the signal is not applied to the nerve as described herein.

In some embodiments, subjects receive an implantable component 104. (FIG. 1) The electrodes 212, 212a are placed on the anterior vagus nerve AVN and posterior vagus nerve PVN just below the patient's diaphragm. The external antenna (coil 102) is placed on the patient's skin overlying the implanted receiving coil 105. The external control unit 101 can be programmed for various signal parameters including options for frequency selection, pulse amplitude and duty cycle. For blocking signals, the frequency options include 2500 Hz and 5000 Hz (both well above a threshold blocking frequency of 200 Hz). The vast majority of treatments are at 5,000 Hz, alternating current signal, with a pulse width of 100 microseconds. The amplitude options include 1-18 mA. For stimulating signals, a frequency is selected of less than 200 Hz.

Duty cycle could also be controlled. A representative duty cycle is 5 minutes of blocking frequency followed by 5 minutes of no signal. The duty cycle is repeated throughout use of the device.

Figure 5:
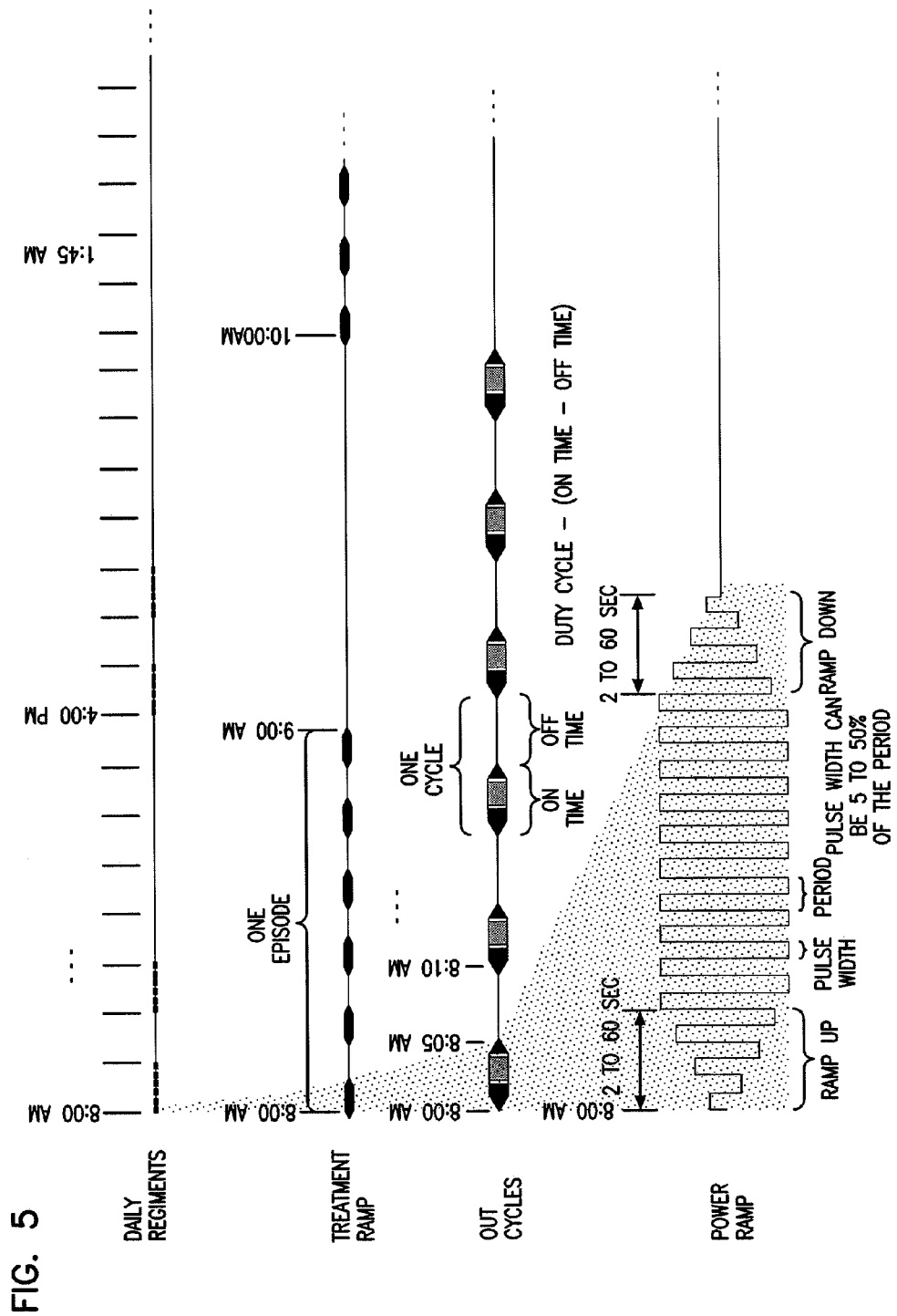
FIG. 5 shows a typical duty cycle.

FIG. 5 shows an exemplary duty cycle. Each ON time includes a ramp-up where the 5,000 Hz signal is ramped up from zero amperes to a target of 6-8 mA. Each ON time further includes a ramp-down from full current to zero current at the end of the ON time. For about 50% of the patients, the ramp durations were 20 seconds and for the remainder the ramp durations were 5 seconds. In some embodiments, the on time is elected to have a duration of no less than 30 seconds or no more than 180 seconds or both. The duration of the on time is selected to provide for at least partial blocking or down-regulation of the neural activity. The off time is selected to provide for at least partial recovery of neural activity.

The use of ramp-ups and ramp-downs are conservative measures to avoid possibility of patient sensation to abrupt application or termination of a full-current 5,000 Hz signal.

In some embodiments, a mini duty cycle can be applied. In an embodiment, a mini duty cycle comprises 180 millisecond periods of mini-ON times of 5,000 Hz at a current which progressively increases from mini-ON time to mini-ON time until full current is achieved (or progressively decreases in the case of a ramp-down). Between each of such mini-ON times, there is a mini-OFF time which can vary but which is commonly about 20 milliseconds in duration during which no signal is applied. Therefore, in each 20-second ramp-up or ramp-down, there are approximately one hundred mini-duty cycles, having a duration of 200 milliseconds each and each comprising approximately 180 milliseconds of ON time and approximately 20 milliseconds of OFF time.

Normally a patient would only use the device while awake. The hours of therapy delivery can be programmed into the device by the clinician (e.g., automatically turns on at 5:00 AM and automatically turns off anywhere from 10 pm to 1:00 am). In some cases, the hours of therapy would be modified to correspond to times when blood pressure fluctuates such as during the day. For example, the hours of therapy may be adjusted to start at early in the morning when heart attack and stroke are more likely to occur. In embodiments, the device is configured to deliver therapy no less than 12 hours while the patient is awake.

The treatment time can be an entire 24 hour period, 18 to 24 hours, 16 to 24 hours, 12 to 24 hours, 8 to 24 hours, 6 to 24 hours, 4 to 24 hours, or any interval that provides for patient responsiveness, or combinations thereof. Treatment time may be varied depending on whether the patient experiences a drop in blood pressure while sleeping. Some patients who have hypertension have a blood pressure of greater than or equal to 135/85 mm Hg while they are awake and greater than or equal to 120/75 mm Hg when they are asleep. For those patients, the treatment would not be administered during some of the sleeping hours of the patient. However, in most cases, treatment would resume as early as 4 am in order to avoid the early morning spike in blood pressure which can lead to heart attack or stroke. In other cases, for those patients who do not experience a drop in blood pressure while they are sleeping, treatment may be administered for a full 24 hour period.

In the RF-powered version of the impulse generator, use of the device is subject to patient control. For example, a patient may elect to not wear the external antenna. The device keeps track of usage by noting times when the receiving antenna is coupled to the external antenna through radio-frequency (RF) coupling through the patient's skin.

In some cases, loss of signal contact between the external controller 101 and implanted impulse generator 104 occurs in large part to misalignment between coils 102, 105. It is believed coil misalignment results from, at least in part, changes in body surface geometry throughout the day (e.g., changes due to sitting, standing or lying down). These changes can alter the distance between coils 102, 105, the lateral alignment of the coils 102, 105 and the parallel alignment of the coils 102, 105. Misalignment can be detected by the device and alignment of the coils adjusted by the patient of physician to ensure that the signals are restored. The device may include a notification to the patient or physician if there has been a misalignment.

In some embodiments, the external component 101 can interrogate the impulse generator component 104 for a variety of information. In some embodiments, therapy times of 30 seconds to 180 seconds per duty cycle are preferred to therapy times of less than 30 seconds per duty cycle or greater than 180 seconds per duty cycle.

During a 10 minute duty cycle (i.e., intended 5 minutes of therapy followed by a 5 minute OFF time), a patient can have multiple treatment initiations. For example, if, within any given 5-minute intended ON time, a patient experienced a 35-second ON time and 1.5 minute actual ON time (with the remainder of the 5-minute intended ON time being a period of no therapy due to signal interruption), the patient could have two actual treatment initiations even though only one was intended. The number of treatment initiations varies inversely with length of ON times experienced by a patient.

The flexibility to vary average neural activity, such as vagal activity, gives an attending physician great latitude in treating a patient. For example, in treating hypertension, the blocking signal can be applied with a short "no blocking" time. If the patient experiences discomfort, the duration of the "no blocking" period can be increased to improve patient comfort. The blocking and no blocking duration can be adjusted to achieve patient comfort. Other parameters can be adjusted including current amplitude and frequency.

While patient comfort may be adequate as feedback for determining the proper parameters for duration of blocking and no blocking, more objective tests can be developed. For example, the duration of blocking and no blocking can be adjusted to achieve desired levels of blood pressure control. Such testing can be measured and applied on a per patient basis or performed on a statistical sampling of patients and applied to the general population of patients.

In some embodiments, a sensor may be employed. A sensing electrode SE can be added to monitor neural activity as a way to determine how to modulate the neural activity and the duty cycle. While sensing electrode can be an additional electrode to blocking electrode, it will be appreciated a single electrode could perform both functions. The sensing and blocking electrodes can be connected to a controller as shown in FIG. 1. Such a controller is the same as controller 102 previously described with the additive function of receiving a signal from sensing electrode.

In some embodiments, the sensor can be a sensing electrode, a sensor, or sensor that senses other biological molecules or hormones of interest. A sensor may also be employed to measure heart rate, blood pressure, or cardiac function or any combination thereof. When the sensing electrode SE yields a signal representing a preselected blood pressure (e.g. greater than or equal to 130 mm Hg and/or greater than or equal to 80 mm Hg) or a targeted maximum vagal activity or tone (e.g., 50% of baseline as shown in FIG. 4) the controller with the additive function of receiving a signal from sensing electrode energizes the blocking electrode BE with a blocking signal. As described with reference to controller 102, a controller with the additive function of receiving a signal from a sensing electrode can be remotely programmed as to parameters of blocking duration and no blocking duration as well as targets for initiating a blocking signal.

In some embodiments, of the apparatus and method described herein use recovery of the vagus nerve to control a degree of down-regulation of vagal activity. This gives a physician enhanced abilities to control a patient's therapy for maximum therapeutic effectiveness with minimum patient discomfort.

Agents that Alter Blood Pressure of the Subject

The disclosure provides methods for treating a condition associated with impaired blood pressure and/or heart rate that include administering to a subject a composition comprising an agent that affects blood pressure and/or heart rate in a subject. In some embodiments, the patients may be refractory to one or more pharmaceuticals for treatment of elevated blood pressure. In that case, modulation of vagal nerve activity may be employed without administration of other agents. In other cases, for patients refractory to one or more drugs a combination of modulation of vagal nerve activity with administration of one or more agents may be beneficial. In other embodiments, a drug used to treat a cardiac condition may be associated with hypotensive effects and therefore the drug may be administered with an electrical treatment signal that increases blood pressure.

Agents that affect impaired blood pressure control can be selected based on an ability to complement treatment of applying a signal to alter neural activity of a target nerve. As described herein, an agent is selected that may provide a complementary or synergistic effect with the application of signal to modulate neural activity on a target nerve such as the vagus nerve. A synergistic or complementary effect can be determined by determining whether the patient has an improvement in blood pressure and/or heart rate as described herein as compared to one or both treatments alone.

In some embodiments, agents that act at a different site or through a different pathway may be selected for use in the methods described herein. Agents that complement treatment are those that include a different mechanism of action for affecting the heart rate and/or blood pressure control of the subject.

An agent may also or in addition be selected to be administered that may have undesirable side effects at the recommended dosage that prevents use of the agent, or that provides inadequate blood pressure control. In addition, patients that have cardiac conditions, liver disease, or renal disease may not be able to tolerate treatment with one or more of the agents at the recommended dosage due to adverse side effects.

Combining administration of a drug with undesirable side effects with modulating neural activity on a target nerve may allow for administration of the drugs at a lower dose thereby minimizing the side effects, may allow for administration of a single drug instead of multiple drugs, or may allow administration of higher doses of the drugs. In addition, a drug may be selected that has altered pharmacokinetics when absorption is slowed by a delay in gastric emptying due to neural downregulation as described herein. In other embodiments, the recommended dosage may be lowered to an amount that has fewer adverse side effects. In embodiments, it is expected that the recommended dosage may be able to be lowered at least 25%. In other embodiments, the dosage can be lowered to any percentage of at least 25% or greater of the recommended dose. In some embodiments, the dosage is lowered at least 25, 30, 35, 40, 45, 50, 55, 60, 65, 70, 75, 80, 85, 90, 95, or 100% of the recommended dosage.

In an embodiment, a method provides a treatment for a condition associated with impaired blood pressure and/or heart rate. Conditions associated with impaired blood pressure and/or heart rate includes, hypertension, prehypertension, congestive heart failure, ischemic heart disease, coronary artery disease, chronic renal disease, and cerebral vascular disease. A method comprises selecting a drug useful for treating hypertension or congestive heart failure and having a recommended dosage for efficacy where a patient is likely to experience disagreeable side effects at said recommended dosage; and treating the patient with a concurrent treatment comprising: applying an intermittent neural block to a target nerve of the patient at multiple times per day and over multiple days with the block selected to down-regulate afferent and/or efferent neural activity on the nerve and with neural activity restoring upon discontinuance of said block; and administering said drug to the patient at a dosage less than said recommended dosage. In some embodiments, the effective dosages for such a patient are associated with disagreeable side effects contributing to said patient not complying with a drug treatment. In some embodiments, patients are those that have cardiac conditions, liver, or renal disorder and may not be able to tolerate treatment with one or more of the agents.

A method comprises selecting a drug useful for treating a cardiac condition and having a recommended dosage for efficacy where a patient is likely to experience disagreeable side effects at said recommended dosage such as hypotension; and treating the patient with a concurrent treatment comprising: applying an intermittent neural conduction signal to a target nerve of the patient at multiple times per day and over multiple days with the signal selected to up-regulate neural activity and with neural activity restoring upon discontinuance of said signal; and administering said drug to the patient at a dosage less than said recommended dosage. In embodiments, the target nerve is the vagus nerve at a location below vagal innervation of the heart.

A number of oral and parenteral medications are available for the treatment of hypertension. Some of these medications are also commonly employed for the treatment of congestive heart failure.

Beta-blockers (beta-adrenergic blockers) work by reducing sympathetic nerve input to the heart. Thus, the heart beats less often per minute and with less force. Subsequently, the heart reduces its work, and blood pressure drops. Beta-blockers include propranolol, metoprolol, atenolol, and many others. Alpha-blockers (alpha-adrenergic blockers) target the nervous system to relax blood vessels, allowing blood to pass more easily. Examples of alpha blockers are doxazosin, prazosin, and terazosin. Alpha-beta-blockers (alpha- and beta-adrenergic blockers) basically have the same effect as a combined alpha-blocker and beta-blocker. They target the nervous system to relax the blood vessels, as well as work to slow the heartbeat. As a result, less blood is pumped through wider vessels, decreasing the overall blood pressure. Alpha-beta-blockers include labetalol and carvedilol.

Diuretics cause the body to excrete water and salt. This leads to a reduction in plasma volume, which subsequently lowers systemic blood pressure. Diuretics include furosemide, hydrochlorothiazide, and spironolactone.

Angiotensin Converting Enzyme (ACE) inhibitors work by preventing the body's production of angiotensin II, a hormone that normally causes blood vessels to narrow. Consequently, the vessels remain wider, which lowers blood pressure. Angiotensin II also normally stimulates the release of another hormone, called aldosterone, which is responsible for the body's retention of sodium. Hence, in addition to creating wider vessels, ACE inhibitors mimic the effect of diuretics to a certain extent. As a result, blood vessels are subject to less pressure, and the heart performs less work. Examples of ACE inhibitors include enalapril, captopril, and lisinopril. Angiotensin II antagonists are primarily used for patients who develop a cough as a side effect of taking ACE inhibitors. This medication antagonizes angiotensin II, thus inhibiting its effects. Examples include losartan and valsartan.

Calcium channel blockers keep calcium from entering the muscle cells of the heart and blood vessels. The heart and vessels relax, allowing blood pressure to go down. Some calcium channel blockers are nifedipine, verapamil, and diltiazem.

Vasodilators work by relaxing the muscle in the blood vessel wall. Hydralazine and minoxidil are both generic forms of vasodilators.

All drugs used for hypertension or congestive heart failure have side effects. Common side effects include fatigue, coughing, skin rash, sexual dysfunction, depression, cardiac dysfunction, or electrolyte abnormalities. In addition, some of the drugs may not be compatible with other drugs that are administered to people with cardiac problems. Ongoing patient compliance may be difficult. Some clinicians have been concerned about the long-term effects of anti-hypertensive drugs on mental processes.

Dosages for administration to a subject can readily be determined by one of skill in the art. Guidance on the dosages can be found, for example, by reference to other drugs in a similar class of drugs. For example, dosages have been established for any of the approved drugs or drugs in clinical trials and the range of dose will depend on the type of drug. Dosages associated with adverse side effects are known or can also be readily determined based on model studies. A determination of the effective doses to achieve improved blood pressure control while minimizing side effects can be determined by animal or human studies.

Agents will be formulated, dosed, and administered in a fashion consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners. The agent need not be, but is optionally formulated with one or more agents currently used to prevent or treat the disorder in question. The effective amount of such other agents depends on the amount of agent that improves glycemic control of the subject present in the formulation, the type of disorder or treatment, and other factors discussed above. These are generally used in the same dosages and with administration routes as used hereinbefore or about from 1 to 99% of the heretofore employed dosages.

Therapeutic formulations comprising the agent are prepared for storage by mixing the agent having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated. In such embodiments, the compounds have complementary activities that do not adversely affect each other. Such molecules are suitably present in combination in amounts that are effective for the purpose intended.

The therapeutic agent is/are administered by any suitable means, including parenteral, subcutaneous, orally, intradermal, intraperitoneal, and by aerosol. Parenteral infusions include intramuscular, intravenous, intraarterial, intraperitoneal, or subcutaneous administration. Pumps may be utilized as well as drug eluting devices and capsules.

EXAMPLE 1

Material and Methods/Experimental Design

An open-label, prospective, baseline-controlled, four-center clinical study was conducted to evaluate feasibility and safety and efficacy of a device as described herein that causes intermittent electrical blocking of the anterior and posterior vagal trunks. The participating centers included Flinders Medical Centre, Adelaide, Australia; Circle of Care, Sydney, Australia; University Hospital, Basel, Switzerland; and St. Olays University Hospital, Trondheim, Norway.

Patients

Male or female obese subjects (BMI 31.5-55 kg/m$^2$) 25-60 years of age inclusive, were recruited at the four centers. The study assessed device safety and efficacy for 6 months.

Ability to complete all study visits and procedures was an eligibility requirement. Relevant exclusion criteria included: current type 1 diabetes mellitus (DM) or type 2 DM poorly controlled with oral hypoglycemic agents or with associated autonomic neuropathy, including gastroparesis; treatment with weight-loss drug therapy or smoking cessation within the prior three months or reductions of more than 10% of body weight in the previous 12 months; prior gastric resection or other major abdominal surgery, excluding cholecystectomy and hysterectomy; clinically significant hiatal hernias or intra-operatively determined hiatal hernia requiring surgical repair or extensive dissection at esophagogastric junction at time of surgery; and presence of a permanently implanted electrical powered medical device or implanted gastrointestinal device or prosthesis.

Concurrent treatment for thyroid disorders, epilepsy or depression with tricyclic agents was acceptable for participation if the treatment regimen was stable for the prior six months.

Implantation of Device

The device included two electrodes (one for each vagal trunk), a neuroregulator (impulse generator) placed subcutaneously and an external controller to program the device.

Under general anesthesia, two leads (electrodes) of the vagal blocking system (FIG. 4) were implanted laparoscopically. Device implantation by the experienced surgeons participating in the study typically took 60 to 90 minutes; five ports were usually used. The electrode itself had an active surface area of 10 mm$^2$ and was "c"-shaped to partially encircle the nerve.

Intra-abdominal dissection and electrode placement were accomplished in the following sequence. The gastrohepatic ligament was dissected to expose the esophagogastric junction (EGJ), and the stomach was retracted downward and laterally in order to keep slight tension on the EGJ. To locate the posterior vagal trunk, the right diaphragmatic crus was identified and separated from its esophageal attachments. The anterior vagal trunk was identified by locating it as it courses through the diaphragmatic hiatus. After both vagal trunks had been identified, a right angle grasper was used to dissect a 5 mm window underneath the posterior vagal trunk. The electrode was then placed by positioning a right angle grasper through the window that had been created under the vagal trunk. The electrode's distal suture tab was then grasped, and the electrode was pulled into place, seating the nerve within the electrode cup. The same steps were repeated to place a second electrode around the anterior vagal trunk. Finally, each electrode was secured in position using a single suture placed through each electrode's distal suture tab and affixed to the outer layers of the esophagus.

The leads were then connected to the neuroregulator, and it was implanted in a subcutaneous pocket in the mid-line just below the xiphoid process. Proper electrode placement was then determined in two different ways at implant. First, correct anatomic electrode-nerve alignment was verified visually. Secondly, effective electrical contact was verified using impedance measurements intra-operatively and at frequent intervals thereafter. After recovery from the surgery, a programmable external controller which contained a rechargeable power source was used to communicate transdermally with the implanted neuroregulator via an external transmit coil Electrical Signal Application The external controller was programmed for frequency, amplitude and duty cycle. The therapeutic frequency selected to block neural impulses on the vagal trunks was 5000 Hz, based on animal studies of vagal inhibition of pancreatic exocrine secretion. Amplitudes utilized ranged from 1-6 mA; however, in almost all instances, the amplitude was 6 mA. The device was activated in the morning, and turned off before sleep. The protocol specified an algorithm of five minutes of blocking alternating with five minutes without blocking for 12 hours per day. Effective electrical contact was verified using impedance measurements at frequent intervals postoperatively.

Experimental Therapy and Follow-Up Studies

In order to focus on the effects of the vagal blocking system, the study subjects were precluded from receiving either concomitant diet or behavioral counseling or drug therapy for obesity during the 6 month trial period. All study participants were implanted with the device. Two weeks post-implant, intermittent, high-frequency electrical algorithms were commenced in all subjects. Subjects were followed weekly for 4 weeks, then every two weeks until 12 weeks and then monthly visits for body weight, physical examination and adverse event (AE) inquiry. In addition, 12-lead electrocardiograms (ECGs) and clinical chemistries were analyzed at a core laboratory.

Calculation of Percentage Excess Weight Loss

Ideal body weight was calculated by measuring each subject's height and then determining the body weight that would result in a BMI of 25.0 for that subject, i.e., ideal body weight (kg)=25×height$^2$ (m). EWL was calculated by dividing weight loss by excess body weight [(total body weight)–(ideal body weight)] and multiplying by 100. Thus, EWL %=(weight loss (kg)/excess body weight (kg))×100.

Data and Statistical Analysis

Baseline characteristics and demographics were summarized using descriptive statistics. Continuous variables were summarized by mean values and corresponding standard errors of the mean (SEM). Categorical (including binary) variables were summarized by frequency distributions.

The primary endpoint for assessing the effect on weight loss was the mean percent excess weight loss (EWL %) at specified time points (4 and 12 weeks and 6 months) and compared to zero in a two-sided, one-sample t-test at the 5% significance level. P-values reported were unadjusted for multiple comparisons. However, the statistical significance was not altered after applying Hochberg's multiple comparison procedure.

Changes in heart rate and blood pressure were summarized over time, using mean and SEM. ECG recordings were collected and analyzed by an independent core lab (Mayo Medical Laboratories, Rochester, Minn., USA). Endpoints included changes in heart rate (HR), PR interval, QRS duration and QTcB interval (QT interval Bazett correction). ECGs were, in all known instances, recorded with the vagal blocking off to detect sustained effects, if any.

Adverse events (AE) were tabulated and reported. No formal statistical analyses of adverse events were performed on the rate of occurrence of adverse events as no a priori hypotheses were specified.

Results

Participants, Demographics and Outcomes of Surgical Procedure

Thirty-nine subjects (mean body mass index 41.2±4.1 kg/m$^2$) received the device. Demographics are shown in Table I.

TABLE I

| Demographics of study population (mean ± SEM) | |
|---|---|
| Demographics | All subjects |
| Number | 39 |
| Age (yrs) | 41.0 ± 9.8 |
| Gender | 33 female/6 male |
| Baseline BMI, kg/m$^2$ | 41.2 ± 4.1 |

There have been no major intra-operative complications with implantation of the device. Specifically, we have not encountered organ perforation, significant bleeding, post-operative intra-peritoneal infections, or electrode migration or tissue erosion. The devices were left in place after the 6 month study. Those participants continue to be followed as part of a safety cohort for such a device, and further studies are being conducted to determine whether the electrical parameters can be modified to maximize the efficacy of the device.

Weight Loss

Figure 6:
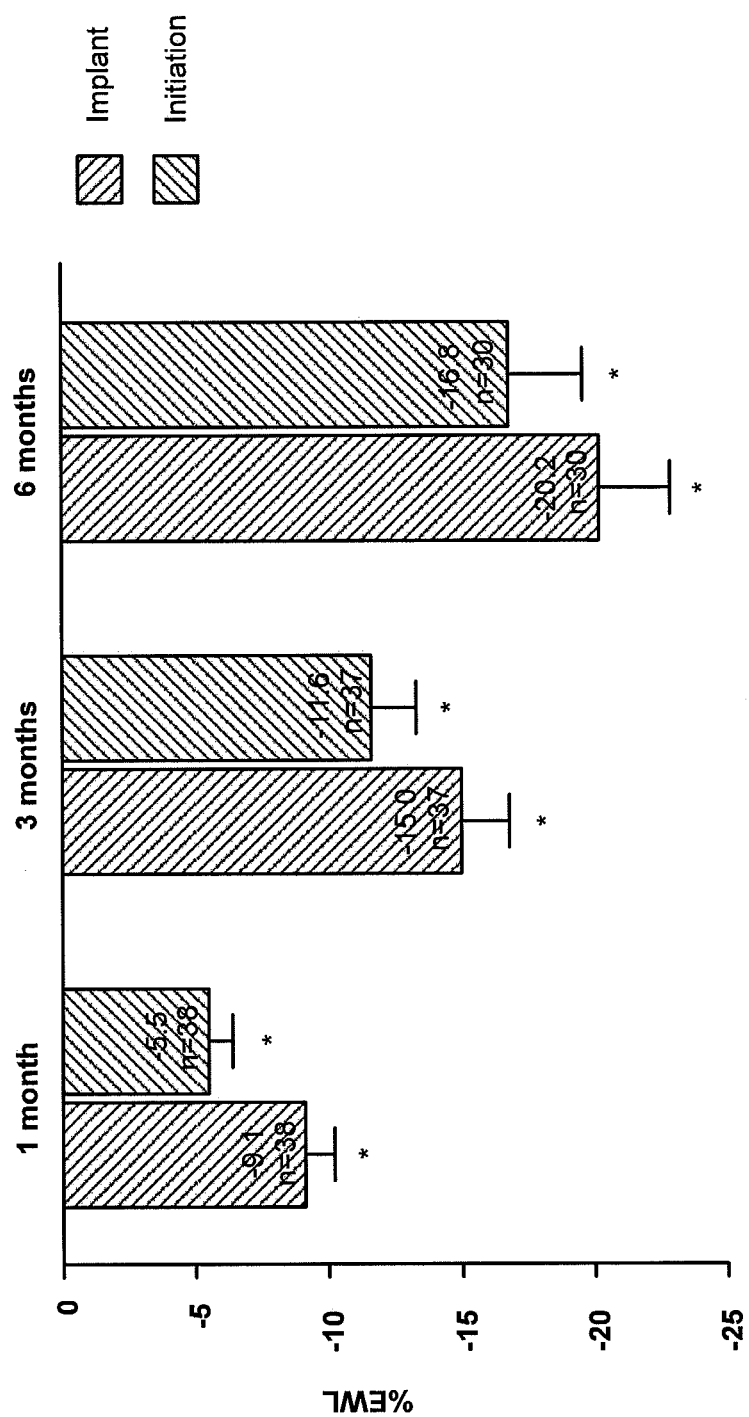
FIG. 6 shows effects of electrical signal therapy on excess weight loss for patients in the study described herein.

Mean excess weight loss at 4 and 12 weeks and 6 months following device implant was 9.1%, 15% and 20.2%, respectively (all changes were significant compared to baseline, p<0.0001). Beneficial overall effects of treatment were observed at all four centers. FIG. 6 shows the distribution of EWL percentage change. A decrease in waist circumference was also observed. Waist circumference was decreased about 6.4+/−1.4 cm at 3 month and 7.8 cm+/−1.7 cm at six months from a mean baseline of 123.4 cm.

Adverse Events

There were no deaths, no serious adverse events (SAE) related to either the medical device or the electrical signal therapy and no unanticipated adverse device effects during the study. Three subjects, who had SAEs that were unrelated to the device or with vagal blocking therapy, required brief hospitalization: one post-operative lower respiratory tract infection (1 day hospitalization), one subcutaneous implant site seroma (3 days hospitalization), and one case of *Clostridium difficile* diarrhea two weeks into the trial period (5 days hospitalization). These three SAEs were completely reversible, and the patients continued in the study.

Effects on Heart Rate and Blood Pressure

Patients were also evaluated for changes in heart rate and blood pressure.

Figure 7A:
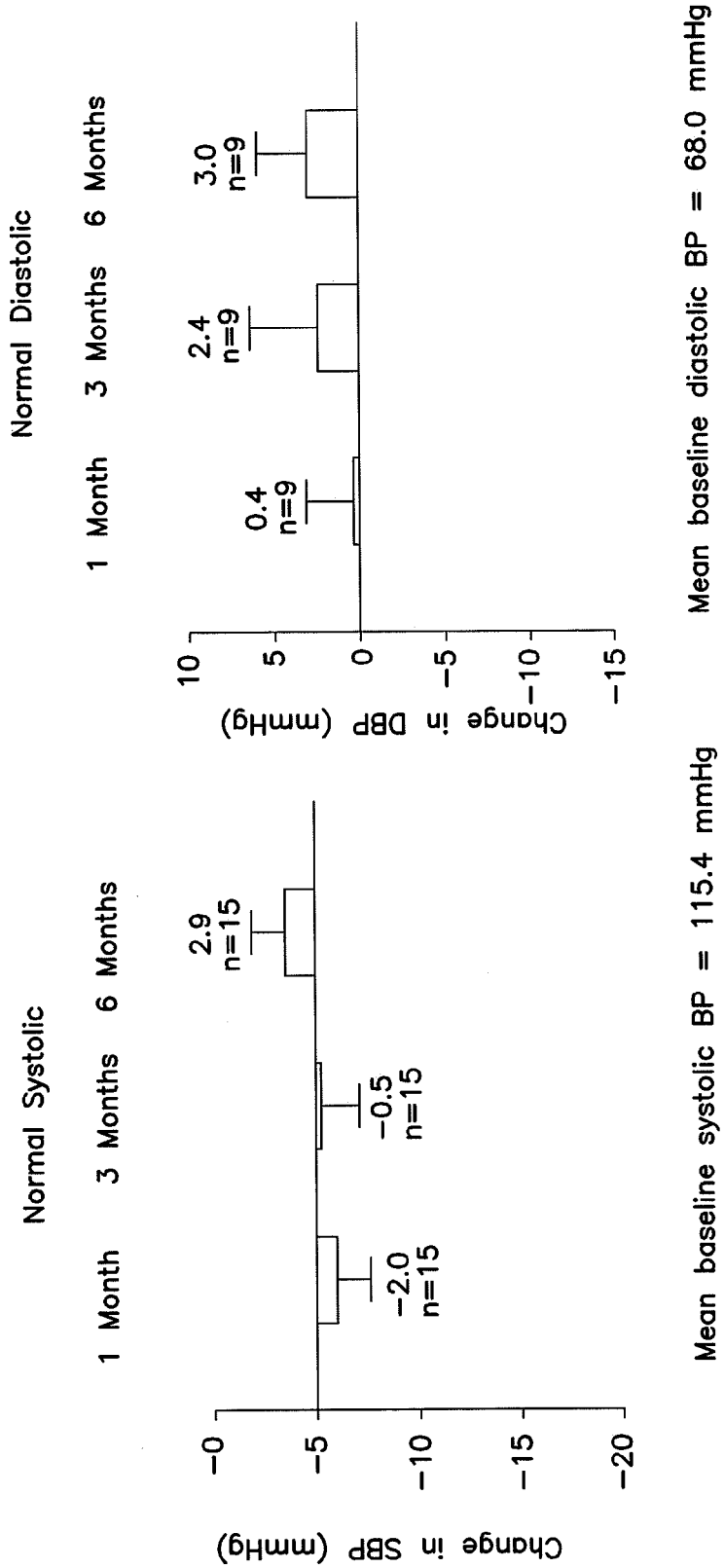
FIG. 7A shows the effect of electrical signal therapy on blood pressure for subjects receiving treatment and who did not have elevated blood pressure at the start of treatment and completed 6 months of therapy. The mean baseline systolic pressure was 115.4 mmHg and the mean baseline diastolic pressure was 68.0 mm Hg. No significant changes were seen in subjects with normal baseline systolic blood pressure (SBP) and diastolic blood pressure (DBP) at 1, 3 or 6 months.
Figure 7B:
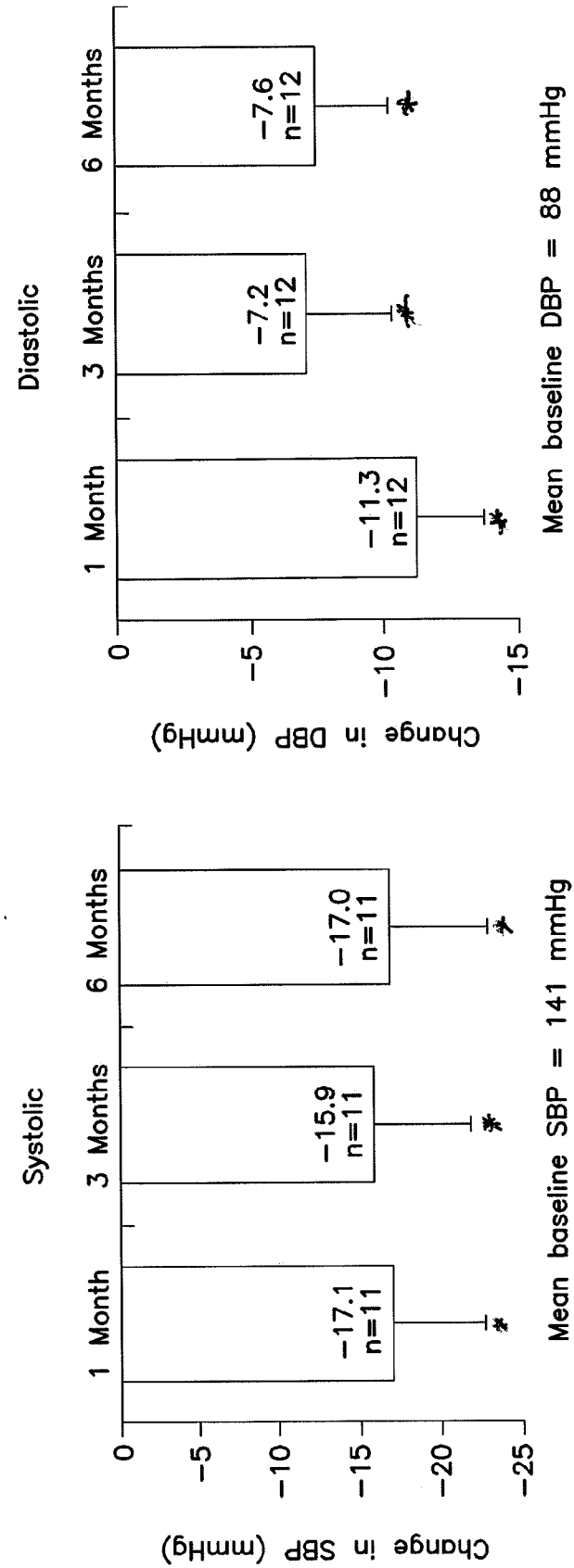
FIG. 7B shows the effect of electrical signal therapy on the change in blood pressure for subjects with elevated blood pressure completing 6 months of therapy. The cohort was defined by elevated systolic pressure of greater than or equal to 140 mmHg or diastolic blood pressure of greater than or equal to 90 mmHg or a history of hypertension. The mean baseline systolic pressure was 141 mmHg and the mean baseline diastolic pressure was 88 mm Hg. Significant changes were seen in subjects with hypertensive baseline systolic blood pressure (SBP) and diastolic blood pressure (DBP) at all time points.

When all of the patients that completed 6 months of treatment were evaluated for changes in blood pressure, about a 10% decrease in systolic and diastolic blood pressure was seen over the 6 month period. (data not shown) Some of the patients had normal blood pressure at the initiation of treatment, these patents did not experience any significant effects on blood pressure. Those patients had a mean baseline systolic pressure of 115.4 mm Hg and a mean baseline diastolic pressure of 68.0 mm Hg. No significant change in blood pressure was observed over the treatment time. See FIG. 7A Patients who had elevated blood systolic pressure of greater than or equal to 140 mm Hg and/or diastolic blood pressure greater than equal to 90 mmHg or had a history of hypertension had a mean baseline systolic pressure of 141 mmHg and diastolic pressure of 88 mm Hg before electrical signal treatment. After 6 months of treatment, systolic pressure was decreased 17 mmHg (about 12% decrease) and diastolic pressure was decreased 7.6 mm Hg (about 8.6%) from the mean baseline starting pressures. See FIG. 7B.

Patients who had elevated blood systolic pressure of greater than or equal to 140 mm Hg and/or diastolic blood pressure greater than equal to 90 mmHg and were not diabetic; patients with systolic pressure of greater than or equal to 130 mmHg and/or diastolic pressure of greater than or equal to 80 mm Hg and were diabetic, patients that had a history of hypertension, and patients that had pre-hypertension with a systolic pressure of 120 to 139 mm Hg and/or diastolic pressure of 80 to 90 mm Hg had a mean baseline systolic pressure of 132.6 mmHg and diastolic pressure of 84.6 mm Hg before electrical signal treatment. After 6 months of treatment, systolic pressure was decreased 10.2 mmHg (about 8% decrease) and diastolic pressure was decreased 4.8 mm Hg (about 5.7%) from the mean baseline starting pressures. See FIG. 7C. It should also be noted that patients that had both diabetes and hypertension exhibited significant decreases in systolic and diastolic blood pressure from the mean baseline at the beginning of treatment. (data not shown)

Mean arterial pressure (MAP) in hypertensive subjects also showed reductions at 1, 3, and 6 months. The baseline mean arterial pressure was 101+/−2 mm Hg. At 1 month the MAP was reduced 9+/−3 (p=0.002). At three months, the reduction was 7+/−2 mm Hg (p=0.01). The reduction at 6 months was 6+/−2 (p=0.02).

In another study of hypertension subjects, after 1 week of treatment, significant decreases in systolic pressures, diastolic pressures, and mean arterial pressures were observed. (data not shown)

The results showing the shift in systolic and diastolic blood pressure between patients without elevated blood pressure and those with elevated blood pressure at the 6 month visit are shown in FIG. 8. About 70% of the patients having elevated systolic blood pressure saw a drop in systolic blood pressure to below 130 mmHg. About 40% of the patients with elevated diastolic blood pressure showed a drop in diastolic blood pressure to below 80 mmHg. 6 subjects had a concurrent diagnosis of hypertension and were receiving anti-hypertensive medication. 2 of these 6 had reductions in anti-hypertensive meds and a third discontinued all anti-hypertensive meds; in all these instances, blood pressures remained in the normal range.

The results for evaluation of heart rate over 12 weeks of treatment time are shown in Table 2.

TABLE 2

Heart Rate By Visit and Change from Baseline by Visit

| Visit | N | Mean | Std dev | Std err | Min, Max | 95% CI | p-value |
|---|---|---|---|---|---|---|---|
| Baseline | 15 | 76.73 | 6.63 | 1.71 | 64, 84 | 73.06, 80.40 | |
| Week 1 | 14 | 73.64 | 12.19 | 3.26 | 54, 101 | 66.61, 80.68 | |
| Week 4 | 15 | 70.60 | 11.35 | 2.93 | 52, 93 | 64.31, 76.89 | |
| Week 12 | 15 | 69.80 | 9.52 | 2.46 | 53, 85 | 64.53, 75.07 | |
| Change from BL | | | | | | | |
| Week 1 | 14 | −3.00 | 10.40 | 2.78 | −18, 22 | −9.00, 3.00 | 0.30 |
| Week 4 | 15 | −6.13 | 8.05 | 2.08 | −16, 11 | −10.59, −1.67 | 0.01 |
| Week 12 | 15 | −6.93 | 6.36 | 1.64 | −17, 8 | −10.46, −3.41 | 0.0009 |

To date, 15 of 35 subjects' 12-week ECG data were available for analysis. The results are shown in Tables 3-6.

TABLE 3

PR Interval By Visit and Change from Baseline by Visit

| Visit | N | Mean | Std dev | Std err | Min, Max | 95% CI | p-value |
|---|---|---|---|---|---|---|---|
| Baseline | 15 | 164.87 | 22.54 | 5.82 | 118, 211 | 152.39, 177.35 | |
| Week 1 | 14 | 173.57 | 22.53 | 6.02 | 128, 208 | 160.56, 186.58 | |
| Week 4 | 15 | 164.27 | 16.92 | 4.37 | 138, 196 | 154.90, 173.64 | |
| Week 12 | 15 | 167.33 | 19.67 | 5.08 | 132, 200 | 156.44, 178.23 | |
| *Change from BL* | | | | | | | |
| Week 1 | 14 | 8.07 | 11.54 | 3.08 | −16, 28 | 1.41, 14.73 | 0.02 |
| Week 4 | 15 | −0.60 | 10.87 | 2.81 | −18, 20 | −6.62, 5.42 | 0.83 |
| Week 12 | 15 | 2.47 | 14.93 | 3.85 | −33, 34 | −5.80, 10.73 | 0.53 |

TABLE 4

QRS Duration By Visit and Change from Baseline by Visit

| Visit | N | Mean | Std dev | Std err | Min, Max | 95% CI | p-value |
|---|---|---|---|---|---|---|---|
| Baseline | 15 | 91.20 | 9.31 | 2.40 | 80, 108 | 86.04, 96.36 | |
| Week 1 | 14 | 92.14 | 9.92 | 2.65 | 76, 114 | 86.41, 97.87 | |
| Week 4 | 15 | 90.53 | 9.13 | 2.36 | 74, 112 | 85.48, 95.59 | |
| Week 12 | 15 | 91.33 | 9.49 | 2.45 | 74, 108 | 86.08, 96.59 | |
| *Change from BL* | | | | | | | |
| Week 1 | 14 | 0.43 | 4.48 | 1.20 | −6, 10 | −2.16, 3.02 | 0.73 |
| Week 4 | 15 | −0.67 | 4.86 | 1.26 | −8, 8 | −3.36, 2.03 | 0.60 |
| Week 12 | 15 | 0.13 | 7.26 | 1.87 | −9, 22 | −3.89, 4.15 | 0.94 |

TABLE 5

QT Interval By Visit and Change from Baseline by Visit

| Visit | N | Mean | Std dev | Std err | Min, Max | 95% CI | p-value |
|---|---|---|---|---|---|---|---|
| Baseline | 15 | 380.27 | 23.89 | 6.17 | 352, 435 | 367.04, 393.50 | |
| Week 1 | 14 | 378.93 | 29.66 | 7.93 | 323, 441 | 361.80, 396.05 | |
| Week 4 | 15 | 387.53 | 26.16 | 6.75 | 350, 443 | 373.05, 402.02 | |
| Week 12 | 15 | 389.80 | 25.76 | 6.65 | 356, 441 | 375.53, 404.07 | |
| *Change from BL* | | | | | | | |
| Week 1 | 14 | −0.79 | 18.06 | 4.83 | −36, 37 | −11.21, 9.64 | 0.87 |
| Week 4 | 15 | 7.27 | 22.26 | 5.75 | −38, 43 | −5.06, 19.59 | 0.23 |
| Week 12 | 15 | 9.53 | 13.73 | 3.54 | −12, 44 | 1.93, 17.13 | 0.02 |

TABLE 6

QTc Bazett By Visit and Change from Baseline by Visit

| Visit | N | Mean | Std dev | Std err | Min, Max | 95% CI | p-value |
|---|---|---|---|---|---|---|---|
| Baseline | 15 | 428.73 | 19.95 | 5.15 | 398, 469 | 417.68, 439.78 | |
| Week 1 | 14 | 416.14 | 17.50 | 4.68 | 381, 445 | 406.04, 426.25 | |
| Week 4 | 15 | 417.33 | 22.46 | 5.80 | 393, 465 | 404.90, 429.77 | |
| Week 12 | 15 | 417.87 | 18.34 | 4.73 | 389, 456 | 407.71, 428.02 | |
| *Change from BL* | | | | | | | |
| Week 1 | 14 | −11.64 | 25.82 | 6.90 | −88, 21 | −26.55, 3.27 | 0.12 |
| Week 4 | 15 | −11.40 | 23.14 | 5.97 | −43, 44 | −24.21, 1.41 | 0.08 |
| Week 12 | 15 | −10.87 | 19.34 | 4.99 | −39, 35 | −21.58, −0.16 | 0.047 |

Compared with baseline, HR decreased a mean 6.9 bpm (p<0.001), consistent with observed weight loss. Mean PR interval and QRS duration were unchanged (+2.5 msec, p=0.53 and +0.13 msec, p=0.94, respectively). Mean QTcB changed −10.9 msec (p=0.05), consistent with HR changes and not deemed clinically significant.

Discussion

In this clinical trial of an implantable system that delivers intermittent vagal blocking (electrical signal therapy), we report here on safety and efficacy—as measured by EWL %. The % EWL shows that the patients had 20% EWL after 6 months of treatment. In addition, the sub-studies conducted have shown that the weight loss is associated with decreased blood pressure in patients with elevated blood pressure.

Weight reduction observed in this study was progressive out to 6 months of follow-up without an apparent plateau. It is important to note that this effect on weight was achieved without the additional benefit of dietary or behavioral modification, which may augment weight reduction with any intervention. While we cannot completely exclude a placebo effect, given the open trial design, we expect that this is unlikely since the reduced caloric intake, time to satiation at meals and hunger between meals were achieved early after onset of treatment, were maintained throughout the 6 month study, and were associated with significant and sustained weight loss.

Safety of the novel device and electrical signal applied as described herein is supported by the fact that the only notable complications were three infections related to the surgical procedure or *C. difficile* diarrhea, all of which were considered by an independent data safety monitoring committee to be unrelated to the device itself. There were no major intra-operative complications. Specifically, we did not encounter organ perforation or significant bleeding. Furthermore, we did not observe post-operative intra-peritoneal infections, electrode migration or tissue erosion.

The present studies provide some insights on the mechanism for the weight loss associated with electrical signal therapy. The vagus nerve has pivotal roles in multiple aspects of organ function. Changes in cardiovascular parameters such as decreases in blood pressure and heart rate for those patients that have elevated blood pressure are in further support of the efficacy and safety of this treatment. Patients without hypertension or without prehypertension did not have any significant change in blood pressure over the treatment period. Although the current sample size is small, the effects on blood pressure and heart rate are important to note since the vagus is a prominent regulator of parasympathetic tone on the cardiovascular system at the thoracic level. The intermittent vagal blockade is applied at the sub-diaphragmatic level and is effective to reduce blood pressure without adversely affecting other cardiac functions as evidenced by the ECG parameters or without other side effects. In some cases, the treatment was effective to normalize blood pressure and allow patients to discontinue drug treatment. In other cases, the treatment provided for a reduction in the medication that the patients were taking.

Based on the findings from this clinical trial, it can be concluded that intermittent, intra-abdominal vagal blocking using a novel, programmable medical device is associated with both significant excess weight loss and a desirable safety profile. Furthermore, study data support the therapeutic rationale of intermittent, intra-abdominal vagal blocking for treatment of hypertension, congestive heart failure, and/or other conditions that have hypertension as a component.

With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto.

In the sections of this application pertaining to teachings of the prior art, the specification from prior art patents is substantially reproduced for ease of understanding the embodiment of the present invention. For the purpose of the present application, the accuracy of information in those patents is accepted without independent verification. Any publications referred to herein are hereby incorporated by reference.

What is claimed is:

1. A method of treating hypertension or congestive heart failure in a subject comprising:
  applying an intermittent electrical treatment signal to a vagus nerve or tissue in proximity to the vagus nerve at a subdiaphragmatic location of the subject having hypertension or congestive heart failure, wherein said electrical treatment signal is selected to at least partially down-regulate neural activity on the vagus nerve during an on time, have a frequency of about 200 Hz to 25 kHz, and to at least partially restore neural activity on the nerve during an off time.

2. The method according to claim 1, wherein the electrical signal is selected for frequency, pulse width, amplitude, timing and ramp-up/ramp-down characteristics.

3. The method according to claim 1 wherein the on time of the electrical treatment signal is selected to down regulate the neural activity of the nerve at least 50%.

4. The method of claim 1, wherein the electrical signal is applied intermittently in a cycle including an on time of application of the signal followed by an off time during which the signal is not applied to the nerve, wherein the on and off times are applied multiple times per day over multiple days.

5. The method of claim 4, wherein the on time is elected to have a duration of no less than 30 seconds or no more than 180 seconds or both.

6. The method according to claim 1, wherein the electrical signal is applied to an electrode, wherein the electrode is positioned on the vagus nerve or on tissue adjacent to the vagus nerve.

7. The method according to claim 1, wherein the electrical signal is applied to an anterior vagus trunk, posterior vagus trunk, or both.

8. The method of claim 1, further comprising applying an up-regulating signal to a baroreceptor.

9. The method of claim 8, wherein the downregulating signal and the upregulating signal are applied at the same time or different time.

10. The method according to claim 1, further comprising administering an agent that improves blood pressure control.

11. The method of claim 10 wherein the agent that improves blood pressure control is selected from the group consisting of a diuretic, ACE inhibitor, calcium channel blocker, beta blocker, alpha blocker and mixtures thereof.

12. A method of treating hypertension or congestive heart failure comprising:
  a) selecting a drug for treating hypertension for a patient where effective dosages for treating hypertension for such a patient are associated with disagreeable side effects or inadequate blood pressure control; and treating a patient for hypertension with a concurrent treatment comprising:
    i) applying an intermittent electrical treatment signal to a vagus nerve of the patient at multiple times per day and over multiple days with the electrical treatment signal selected to down-regulate afferent and/or efferent neural activity on the nerve, have a frequency of about 200 Hz to 25 kHz, and with neural activity at least partially restoring upon discontinuance of said block; and
    ii) administering said drug to the patient.

13. A system comprising:
  a) an electrode adapted to be placed on a vagus nerve at a subdiaphragmatic location;
  b) an implantable neuroregulator connected to the electrode and configured to deliver an electrical signal to the vagus nerve, wherein the electrical signal is i) delivered with a duty cycle of an on time and an off time multiple times in a day ii) has a frequency of 200 to 5000 Hz selected to down regulate neural activity on the nerve during an on time, iii) has an off time selected to provide for at least partial recovery of nerve function, and iv) has an amplitude of at least 6 mA;

c) an external coil, wherein the external coil is configured to communicate data and power signals to the neuroregulator and to communicate data to another programming device; and d) a sensor that is configured to sense blood pressure and to send a signal to the neuroregulator to deliver the electrical signal if the blood pressure becomes pre hypertensive or greater.

14. The system of claim 13, wherein the electrode is adapted to be placed on the vagus nerve at a subdiaphragmatic location.

15. The system of claim 13, wherein the neuroregulator is configured to deliver the electrical signal intermittently for a treatment period of no less than 12 hours and no more than 18 hours.

16. The system of claim 13, wherein the neuroregulator is configured to deliver a signal with an on time of 30 seconds to 5 minutes.

17. The system of claim 13, wherein the neuroregulator is configured to deliver an off time of 2 to 20 minutes.

18. The system of claim 13, wherein the amplitude is from about 6 to 18 mA.

* * * * *